(12) United States Patent
Tandon et al.

(10) Patent No.: US 7,611,707 B2
(45) Date of Patent: Nov. 3, 2009

(54) GLYCOPROTEIN VI ANTIBODIES AND METHODS THEREOF

(75) Inventors: Narendra Nath Tandon, Gaithersburg, MD (US); Yutaka Matsumoto, Naruto (JP); Hisao Takizawa, Tokushima (JP); Keiji Okuyama, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 29 days.

(21) Appl. No.: 11/578,562

(22) PCT Filed: Apr. 26, 2005

(86) PCT No.: PCT/US2005/014109

§ 371 (c)(1),
(2), (4) Date: Oct. 16, 2006

(87) PCT Pub. No.: WO2005/111083

PCT Pub. Date: Nov. 24, 2005

(65) Prior Publication Data

US 2007/0202108 A1 Aug. 30, 2007

Related U.S. Application Data

(60) Provisional application No. 60/566,171, filed on Apr. 29, 2004.

(51) Int. Cl.
*A61K 39/395* (2006.01)
(52) U.S. Cl. .............. 424/143.1; 424/133.1; 424/141.1; 424/153.1; 530/387.3; 530/388.1; 530/388.22; 530/388.7
(58) Field of Classification Search ........................ None
See application file for complete search history.

(56) References Cited

U.S. PATENT DOCUMENTS

| 4,208,479 | A | * | 6/1980 | Zuk et al. ..................... 435/7.9 |
| 5,859,205 | A | * | 1/1999 | Adair et al. .............. 530/387.3 |
| 6,245,527 | B1 | | 6/2001 | Busfield et al. |
| 6,383,779 | B1 | | 5/2002 | Busfield et al. |
| 6,989,144 | B1 | | 1/2006 | Busfield et al. |
| 6,998,469 | B2 | | 2/2006 | Tandon et al. |
| 7,101,549 | B2 | | 9/2006 | Gill et al. |
| 7,291,714 | B1 | | 11/2007 | Busfield et al. |
| 2002/0141992 | A1 | | 10/2002 | Nieswandt |
| 2004/0001826 | A1 | | 1/2004 | Gill et al. |
| 2006/0216291 | A1 | | 9/2006 | Busfield et al. |
| 2007/0071744 | A1 | | 3/2007 | Munch et al. |
| 2007/0172480 | A1 | | 7/2007 | Clemeston |
| 2008/0050380 | A1 | | 2/2008 | Gill et al. |

FOREIGN PATENT DOCUMENTS

| EP | 1 538 165 A1 | 6/2005 |
| WO | WO 00/68377 A1 | 11/2000 |
| WO | WO 01/00810 A1 | 1/2001 |
| WO | WO 0100810 A1 * | 1/2001 |
| WO | WO 02/080968 A1 | 10/2002 |
| WO | WO 03/054020 A2 | 7/2003 |
| WO | WO 03/103662 A2 | 12/2003 |
| WO | WO 2005/007800 A2 | 1/2005 |
| WO | WO 2005/054294 A2 | 6/2005 |

OTHER PUBLICATIONS

Janeway et al., Immunobiology, 3rd edition, Garland Press, 1997, pp. 3:7-3:11.*
Rudikoff et al., Proc Natl Acad Sci U S A. Mar. 1982;79(6):1979-83.*
Schulte et al., J. Biol. Chem., 2001, 276:364-368.*
Portolano et al., J Immunol. Feb. 1, 1993;150(3):880-7.*
Padlan, E.A., Mol Immunol. Feb. 1994;31(3):169-217.*
Gruner, S., et al., Relative antithrombotic effect of soluble GPVI dimer compared with anti-GPVI antibodies in mice, Blood 105(4):1492-9 (2005).
Lecut, C., et al., Identification of residues within human glycoprotein VI involved in the binding to collagen: evidence for the existence of distinct binding sites, J. Biol. Chem. 279(50):52293-9 (2004).
Smethurst, P.A., et al., Identification of the primary collagen-binding surface on human glycoprotein VI by site-directed mutagenesis and by a blocking phage antibody, Blood 103(3):903-11 (2004).
P. Declerck, et al., "Generation of Monoclonal Antibodies against Autologous Proteins in Gene-inactivated Mice", The Journal of Biological Chemistry, vol. 270, No. 15., pp. 8397-8400 (1995).
K. Kato, et al., "The contribution of glycoprotein VI to stable platelet adhesion and thrombus formation illustrated by targeted gene deletion," Blood, vo. 102, No. 5, pp. 1701-1707 (2003).
M. Qian et al., "Anti GPVI human antibodies neutralizing collagen-induced platelet aggregation isolated from a combinatorial phage display library", Human antibodies, vol. 11, No. 3, pp. 97-105 (2002).
J. Davies, et al., "Affinity improvement of single antibody VH domains: residues in all three hypervariable regions affect antigen binding", Immunotechnology, vol. 2, No. 3, pp. 169-179 (1996).

* cited by examiner

Primary Examiner—Michael Szperka
(74) Attorney, Agent, or Firm—Finnegan, Henderson, Farabow, Garrett & Dunner, L.L.P.

(57) ABSTRACT

The present invention describes antibodies generated against platelet membrane glycoprotein VI-(GPVI), methods of producing the anti-GPVI antibodies, and the use of these antibodies as research and immunotherapeutic agents, in particular, as antithrombotic therapeutic agents.

8 Claims, 16 Drawing Sheets

Figure 13
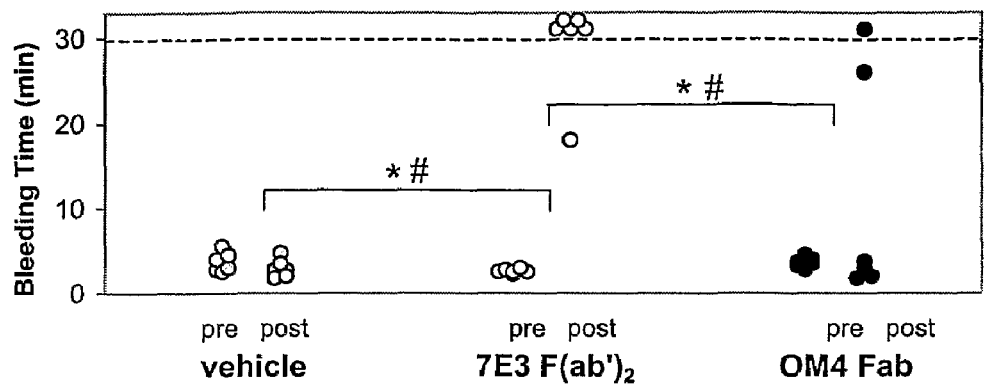
Figure 13A
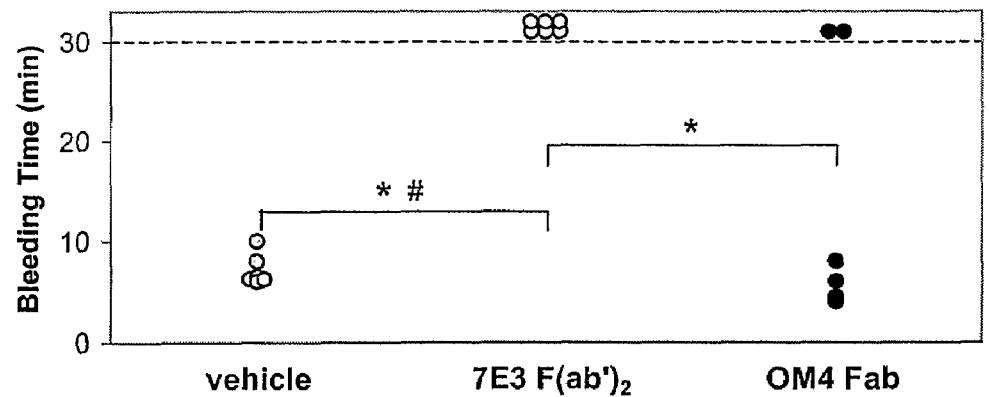
Figure 13B

Figure 15
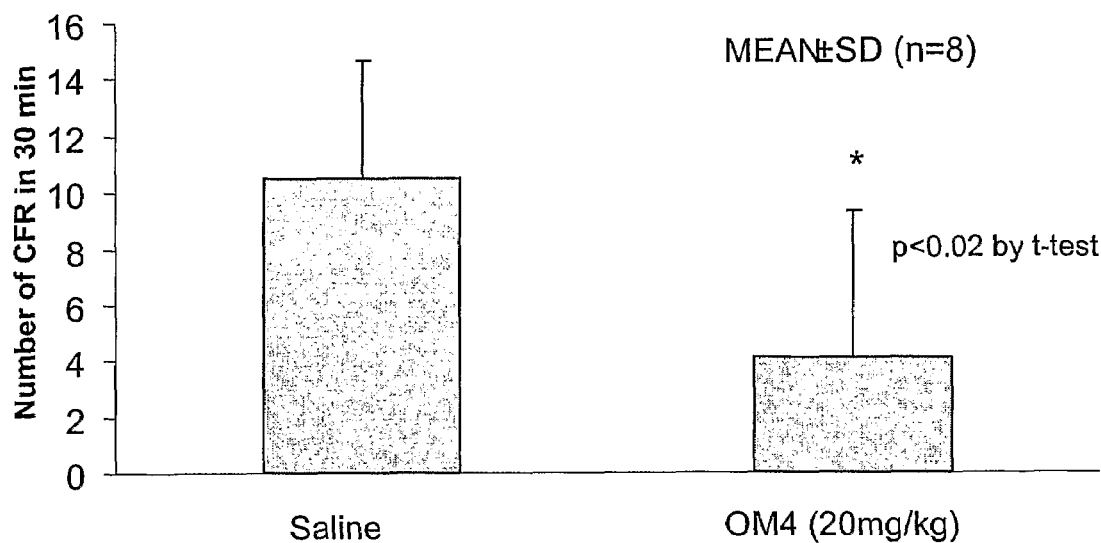
Figure 15A
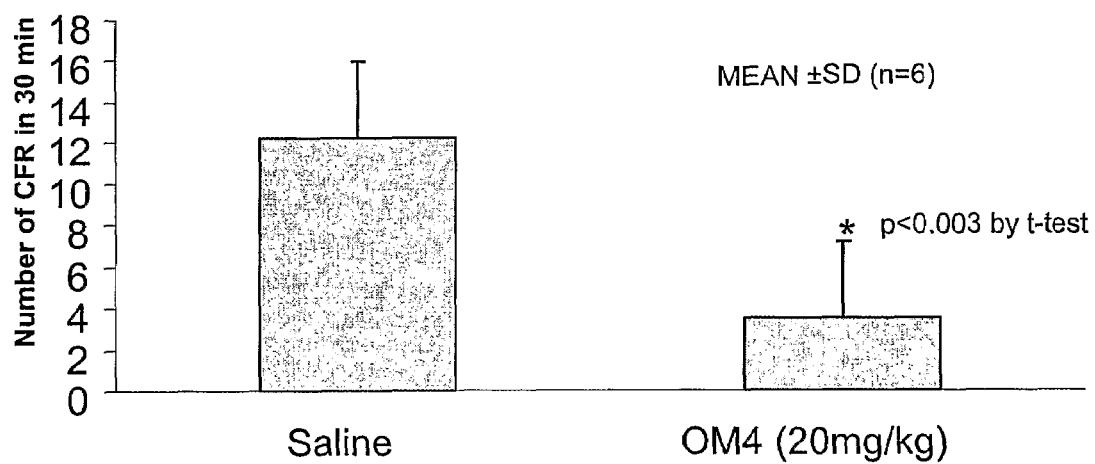
Figure 15B

SEQUENCE LISTING

<160> NUMBER OF SEQ ID NOS: 24

<210> SEQ ID NO 1
<211> LENGTH: 5
<212> TYPE: PRT

```
<213> ORGANISM: Artificial Sequence
<220> FEATURE:
<223> OTHER INFORMATION: Description of Artificial Sequence: Synthetic
      antibody fragment

<400> SEQUENCE: 1

Ser Tyr Trp Met Asn
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody fragment

<400> SEQUENCE: 2

Met Ile His Pro Ser Asp Ser Glu Thr Thr Leu Asn Gln Lys Phe Lys
1               5                   10                  15

Asp

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      antibody fragment

<400> SEQUENCE: 3

Asp Asp Tyr Tyr Asp Ser Ser Ser His Ala Leu Asp Tyr
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      antibody fragment

<400> SEQUENCE: 4

Arg Ala Ser Gln Ser Val Ser Thr Ser Thr Tyr Ser Tyr Ile Tyr
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      antibody fragment

<400> SEQUENCE: 5

Phe Ala Ser Tyr Leu Glu Ser
1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      antibody fragment

<400> SEQUENCE: 6
```

```
Gln His Ile Trp Glu Ile Pro Trp Thr Phe
1               5                   10

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence:  Synthetic
      antibody fragment

<400> SEQUENCE: 7

Asp His Tyr Ile Ser
1               5

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence:  Synthetic
      antibody fragment

<400> SEQUENCE: 8

Trp Ile Tyr Pro Gly Tyr Gly Asn Ile Arg Tyr Asn Glu Lys Phe Lys
1               5                   10                  15
Gly

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence:  Synthetic
      antibody fragment

<400> SEQUENCE: 9

Ser Ala Asp Gly Tyr Phe Arg Tyr Phe Asp Val
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence:  Synthetic
      antibody fragment

<400> SEQUENCE: 10

Arg Ala Ser Gly Asn Ile His Asn Tyr Leu Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence:  Synthetic
      antibody fragment

<400> SEQUENCE: 11

Asn Ser Glu Ile Leu Ala Asp
1               5

<210> SEQ ID NO 12
<211> LENGTH: 10
<212> TYPE: PRT
```

```
<213> ORGANISM: Artificial Sequence
<220> FEATURE:
<223> OTHER INFORMATION: Description of Artificial Sequence:  Synthetic
      antibody fragment

<400> SEQUENCE: 12

Gln His Phe Trp Thr Ala Pro Phe Thr Phe
1               5                   10

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence:  Synthetic
      antibody fragment

<400> SEQUENCE: 13

Asp Phe Tyr Met Asn
1               5

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence:  Synthetic
      antibody fragment

<400> SEQUENCE: 14

Ser Ile Ser Gly Gly Ser Ser Asp Ile Ala Asp Val Val Lys Gly
1               5                   10                  15

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence:  Synthetic
      antibody fragment

<400> SEQUENCE: 15

Trp Gly Asp His Trp Asp Leu Asp Tyr
1               5

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence:  Synthetic
      antibody fragment

<400> SEQUENCE: 16

Gln Ala Ser Gln Asn Ile Gly Asn Glu Leu Asn
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence:  Synthetic
      antibody fragment

<400> SEQUENCE: 17

Gly Ala Ser Ser Leu Tyr Pro
1               5
```

```
<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      antibody fragment

<400> SEQUENCE: 18

Lys Gln Asp Leu Asn Tyr Pro Ile Thr Phe
1               5                   10

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      antibody fragment

<400> SEQUENCE: 19

Ser Phe Gly Met His
1               5

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      antibody fragment

<400> SEQUENCE: 20

Phe Ile Ser Ser Gly Ser Ser Thr Ile Tyr Tyr Ala Asp Ile Val Lys
1               5                   10                  15

Gly

<210> SEQ ID NO 21
<211> LENGTH: 9
<212> TYPE: PRT
<213> ORGANISM: Artificial Sequence
    <220> FEATURE:
<223> OTHER INFORMATION: Description of Artificial Sequence: Synthetic
      antibody fragment

<400> SEQUENCE: 21

Ser Gly Tyr Ala Asn Ala Met Asp Tyr
1               5

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      antibody fragment

<400> SEQUENCE: 22

Lys Ala Ser Gln Asp Val Ser Pro Ala Val Thr
1               5                   10

<210> SEQ ID NO 23
<211> LENGTH: 7
<212> TYPE: PRT
<213> ORGANISM: Artificial Sequence
```

```
<220> FEATURE:
<223> OTHER INFORMATION: Description of Artificial Sequence:  Synthetic
      antibody fragment

<400> SEQUENCE: 23

Trp Ala Ser Thr Arg His Thr
1               5

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence:  Synthetic
      antibody fragment

<400> SEQUENCE: 24

Gln Gln His Tyr Ser Phe Pro Trp Thr Phe
1               5                   10
```

GLYCOPROTEIN VI ANTIBODIES AND METHODS THEREOF

This application claims the benefit of priority to U.S. Provisional Application No. 60/566,171, filed Apr. 29, 2004, which is incorporated herein by reference.

DESCRIPTION OF THE INVENTION

1. Field of the Invention

The present invention relates to antibodies generated against platelet membrane glycoprotein VI (GPVI), fragments, or naturally-occurring variants thereof, to methods of producing the anti-GPVI antibodies, and to the use of these antibodies as research and immunotherapuetic agents, in particular, as therapeutic agents for treating thrombosis and other vascular diseases.

2. Background of the Invention

Platelets are small, a nuclear blood cells that are essential to hemostatic control and wound healing. Circulating platelets are fairly quiescent under normal conditions. However, when a blood vessel is torn or damaged, platelets are exposed to various factors that instigate complicated and interconnected cellular programs leading to blood coagulation and clot formation, which are reviewed in Mechanisms of Platelet Activation and Control, K. S. Authi, S. P. Watson, and V. V. Kakar (eds.) Plenum Press, 1993. The activation of these cellular programs result in dramatic increases in membrane adhesive properties, platelet aggregation, and the release of vasoconstrictive and fibrinolytic factors. As a consequence, a clot forms at the site of trauma, plugging any breach in the vessel wall and providing a substrate for fibroblast invasion and repair.

The early events in the clotting process can be functionally separated into two primary components: adhesion and activation. Adhesion is the process of "sticking" platelets to the injured vascular wall, whereas activation initiates complex physiological changes inside the cell. Together, these two processes result in platelet aggregation, plug formation, and ultimately, in a mature clot. Although these events are crucial in limiting blood loss to the site of injury, platelet adhesion and activation may also contribute to exacerbation of a diseased state. For example, clotting may cause blockage of diseased blood vessels, leading to ischemia and resulting in damage to vital tissues such as the heart and brain. The dual role of platelets in hemostasis and thrombogenesis is reviewed in Ruggeri, Nature Medicine, 8:1227-1234 (2002).

Most steps in these processes depend on the interaction of extracellular ligands with specific receptors embedded in the platelet cell membrane. In vivo, the first visible change in platelet behavior is the adhesion of platelets to an area of denuded endothelium caused by endothelial injury. Among the micromolecular constituents which become exposed at the denuded endothelium, collagen is considered the most reactive with platelets. Collagen supports platelet adhesion through direct and indirect pathways and also activates platelets by initiating platelet aggregation and generating coagulant activity necessary for plug formation. Baumgartner, Thromb Haemost. 37:1-16 (1977).

The initial contact between the platelets and subendothelium involves interaction of the platelet glycoprotein complex GPIb-V-IX with von Willebrand factor (vWf) bound to the exposed subendothelium. This interaction appears to be a reversible process and is insufficient for stable adhesion, as illustrated by "rolling" of platelets along the vessel wall. Ruggeri, Nature Medicine, 8:1227-1234 (2002). Although the vWf interaction does not completely immobilize circulating platelets, it is essential to platelet adherence under high blood flow conditions. Subsequent irreversible binding of platelets to subendothelial collagen through glycoprotein GPIa-IIa (also known as integrin $\alpha_2\beta_1$) stabilizes the vWf interaction event, firmly anchoring the platelet to the vessel wall. Unlike vWf, collagen adhesion appears to be a slower process and is effective only under low flow conditions, or after platelets have been partially arrested by vWf interactions. In addition, GPIa-IIa binding induces the flattening (spreading) of platelet against the vessel wall. Spreading promotes the binding of other subendothelial adhesion factors including fibronectin, vitronectin and thrombospondin. These post-spreading interactions further stabilize the adhesion of platelets to the vessel wall.

GPIa-IIa is an integrin comprising an alpha and beta subunit. In their normal conformation, integrins have low affinity for their natural ligand but may be converted to high affinity receptors through signals generated by other cell receptors Nieswandt B and Watson SP. Blood 102:449-461 (2003). Stimulation of GPIa-IIa and other collagen receptors induces a host of physiological changes. Among these are altered cell surface adhesion properties that result in platelet-platelet aggregation, and the secretion of various bioactive compounds. These compounds include the vasoconstrictor, epinephrine, and proclotting factors, which activate thrombin and lead to polymerization of fibrinogen into the fibrin threads of a mature clot. In addition, activated platelets release ADP and thromboxane $A_2$ ($TXA_2$). These powerful thrombogenic factors amplify the initial activation signal, recruiting additional platelets into the activated state.

In addition to GPIa-IIa, at least two other collagen receptors are expressed on the platelet cell surface, namely, GPIV (CD36), and GPVI (reviewed in Farndale R W et al., J Thromb. Haemost 2:561-573, 2004). Clues to the functions of these platelet collagen receptors have come from the study of human patient variants. Studies of human patient variants suggest that GPVI plays a major role in platelet-collagen interactions while contribution of GPIV remains minor. These studies also showed that a substantial number of individuals lacking either GPIa-IIa or GPVI exhibit slightly prolonged bleeding times than those who express GPIa-IIa or GPVI. Moreover, GPIa-IIa deficiencies generally lead to more severe bleeding disorders than those deficient in GPVI. Nevertheless, these patients rarely present the severe bleeding tendency such as that seen in individuals with Bernard Soulier Syndrome, which is caused by GPIb deficiency, or Glanzmann thrombasthenia, which is caused by GPIIb-IIIa deficiency.

Observations of human variants, along with recent in vitro data, suggest that the three collagen receptors act in concert to mediate collagen-platelet interactions. In vitro, for instance, it is now possible to block the activity of each collagen receptor with antibodies specific for the collagen receptor sites. Individually, each antibody partially inhibits platelet adhesion to collagen and pairwise combinations of antibodies are significantly more inhibitory, particularly when GPIa-IIa and GPVI are inhibited simultaneously. Moreover, these studies demonstrate that GPIV, GPIa-IIa, and GPVI contribute to thrombosis through two distinct pathways, mechanistically distinguishable by the requirement for divalent metal cations.

Biochemical and sequence information indicates that GPIa-IIa is a cation-dependent integrin-type receptor. In contrast, biochemical studies reveal that GPIV and GPVI do not require divalent metal cations and are thus of the non-integrin type. Of the non-integrin class, observations of human subjects clearly suggest that GPVI is more important than GPIV in the primary adhesion process. Indeed, in vitro experiments where GPIa-IIa function is blocked by chelating divalant cations, antibodies directed against GPVI completely abolish collagen-platelet interaction. Nakamura et al. J. Biol. Chem. 273:4338-4344, (1998).

GPVI was first identified about 30 years ago by isoelectric focusing and electrophoresis. Until recently, its function was completely undefined and it was known merely as a platelet glycoprotein with a molecular mass of approximately 62 kDa under reducing condition. However, beginning around 1987, Dr. Minoru Okuma and associates examined several patients with a form of thrombocytopenic purpura, a bleeding/bruising syndrome characterized by accelerated platelet destruction and decreased numbers of circulating platelets. The platelets in some of Dr. Okuma's patients aggregated normally in response to most agonists, including ADP, thrombin, ristocetin, and calcium ionophore (A23187) but were markedly unresponsive to collagen. Moreover, these platelets were found to have reduced amounts, or even totally lack, the 62 kDa glycoprotein. Sugiyama et al., Blood 69:1712-20 (1987); Moroi et al., J. Clin. Invest. 84:1440-45 (1989); Ryo et al., Am. J. Hematol. 39:25-31 (1992); and Arai et al., Brit. J. Haematol. 89:124-130 (1995).

The key reagent in the early studies of GPVI function came from one of Dr. Okuma's thrombocytopenic purpura patients. This patient presented with massive, unexplained bleeding and was treated by transfusion with HLA-matched platelets. Subsequent detailed examination of the patient's blood revealed a total lack of GPVI. Most surprisingly, because this patient totally lacked GPVI, her immune system had identified the GPVI molecules on the transfused platelets as foreign antigens and produced polyclonal antibodies against GPVI. Sugiyama et al., Blood 69:1712-20 (1987).

A naturally occurring antibody is composed of two identical binding sites, specific for a single antigenic epitope. The two antigen-specific portions are linked by a common stem, or Fc domain, to form a complex capable of binding to two identical antigen molecules. Moreover, the divalent nature of the antibody, in conjunction with aggregatory properties of the Fc domain, allow cross-linking and aggregation of many specific antigen molecules. Dr. Okuma found that the divalent antibodies from the patient's serum caused a massive aggregation response when mixed with normal platelets. Conversely, when the antigen-specific domains are rendered monovalent by enzymatic removal of linking Fc domain, the resulting Fab fragments completely abolished collagen-induced aggregation of normal platelets and inhibited platelet-collagen adhesion.

Dr. Okuma has graciously made this rare serum available to the scientific community. Unfortunately, the supply is limited, and the circumstances surrounding its discovery are virtually irreproducible. Although the Okuma serum made possible much of the research into the function of GPVI and had long provided the sole method of identifying a protein as GPVI, it has recently been discovered that the C-type lectin, convulixin, specifically binds to GPVI with high affinity and can be labeled as a probe to identify the GPVI protein. Francishetti et al., Toxicon 35:1217-28 (1997); Polgar et al., J. Biol. Chem. 272(24):13576-83 (1997); Jandrot-Perrus et al., J. Biol. Chem. 272(2):27035-41 (1997). Convulxin is a venom component from the tropical rattlesnake *Crotalus durissus terrificus*. In its native, divalent form, convulxin is a potent inducer of platelet aggregation and secretion of pro-aggregatory and proclotting factors. The divalent nature of convulxin is critical to the aggregatory effect. Although the underlying physiology of the reaction is unclear, individual convulxin subunits still bind to GPVI, but inhibits, rather than induces aggregation. It has been suggested that monovalent convulxin blocks the transmission of collagen-induced signals to the interior of the cell.

Even more recently, the full GPVI sequence was determined. Clemetson et al., J. Biol. Chem. 274:29019-24 (1999); WO 00/68377; Jandrot-Perrus et al., Blood 96:1798-807 (2000); Ezumi et al., Biochem Biophys Res Commun. 277: 27-36 (2000). GPVI belongs to the immunoglobulin super family and is non-covalently associated with the Fc receptor gamma chain (FcRγ chain). Gibbins et al., FEBS Lett. 413: 255-259 (1997); Tsuji et al., J. Biol. Chem. 272:23528-23531 (1997). It is currently believed that collagen binding to GPVI induces tyrosine phosphorylation of FcRγ. Phosphorylated FcRγ then recruits the Syk kinase, ultimately leading to a cascade of intracellular events including phospho-activation of Syk, and phospholipase C-γ2. These events ultimately result in increased intercellular calcium levels and the secretion of proaggregatory and proclotting factors. Therefore, the FcRγ chain serves as the signal-transducing part of the receptor in humans and mouse platelets. Clemetson et al., J. Biol. Chem. 274:29019-290 (1999); Jandrot-Perrus et al., Blood 96:1798-1807 (2000); Gibbins et al., FEBS Lett. 413:255-259 (1997); Tsuji et al., J. Biol. Chem. 272:23528-23531 (1997).

Patients deficient in GPVI suffer from mild bleeding diathesis and their platelets respond poorly to collagen. Sugiyama et al., Blood 69:1712-1720 (1987); Moroi et al., J. Clin. Invest. 84:1140-1445 (1989); Arai et al., Br. J. Haemtol. 89:124-130 (1995). Studies with GPVI-deficient human platelets or platelets blocked with anti-GPVI Fab fragments (obtained from a patient serum) clearly demonstrated a lack of platelet interaction with immobilized collagen under high and low shear rates and reduced firm adhesion to immobilized vWf under high shear. Goto et al., Circulation 106:266-272 (2002).

Studies with knockout mice deficient in the FcRγ chain, which also results in a GPVI-deficient phenotype, or with mice depleted of GPVI, confirmed these observations but these animals exhibited slightly prolonged tail bleeding time. Nieswandt et al., The EMBO Journal 20:2120-2130 (2001). GPVI-deficient, FcRγ-positive mice showed bleeding times similar to those of wild type and GPVI-heterozygous mice. Platelets from the GPVI-deficient mice did not aggregate in response to collagen and to convulxin, and showed dramatically reduced adhesion to immobilized collagen under flow conditions, thereby confirming that GPVI plays a major role in collagen-induced platelet functions and thrombosis. Kato et al., Blood 102:1701-1707 (2003).

It is now accepted that GPVI is the principle receptor for collagen-induced platelet activation, and is a critical conduit for signal transduction. Ichinohe et al., J. Biol. Chem. 270 (47):28029-28036 (1995); Tsuji et al., J. Biol. Chem. 272 (28):23528-31 (1997). In contrast, the other major collagen receptor in platelets, GPIa-IIa, is primarily involved with the cation-dependent processes for effecting stable adhesion and spreading leading to thrombus growth. Reviewed in Nieswandt and Watson, Blood 102:449-461 (2003).

The need in the art for GPVI antagonists, such as antibodies against GPVI, is highlighted by the unfortunate fact that inappropriate platelet aggregation and clot formation is a major etiologic factor in a wide range of human diseases, most commonly, vascular diseases. Excessive platelet deposition on the inner walls of arteries and veins contributes to atherosclerosis and arteriosclerotic plaques, which reduce the flow of blood to sensitive tissues. Ultimately, this platelet-dependent buildup may manifest as acute myocardial infarct, chronic unstable angina, transient ischemia, stroke, peripheral vascular disease, arterial thrombosis, pulmonary embolism, restenosis, and various other conditions.

These conditions typically begin with an abnormal clot that develops in a blood vessel, called a thrombus. Once a clot has developed, continued flow of blood past the clot is likely to break it free from its attachment. Such freely flowing clots are known as emboli. Emboli generally travel through the circulation until trapped in a narrow point in the circulatory system. This occlusion may occur in the brain, lung or coronary arteries, resulting in pain, disability or death.

Intravascular clots may result from naturally-occurring sclerosis, septicemic shock, or physical damage to blood vessels. Indeed, the very invasive methods used to diagnose and treat vascular disease, (e.g. vascular grafts, exploratory and in-dwelling catheters, stents, shunts, and other devices) themselves, damage vessel walls. This can activate platelets, stimulate aggregation, and ultimately lead to the formation of thrombi and emboli, further endangering the life and health of the patient. Thus, methods for controlling or reducing platelet aggregation and clot formation have been a long-sought goal in managing these diseases.

SUMMARY OF THE INVENTION

The present invention provides GPVI specific antibodies that are more potent inhibitors of collagen-induced platelet functions than those previously reported in the art. Thus, the GPVI specific antibodies of the invention may be useful antithrombotic agents and may have reduced side effects often associated with administration of other antithrombotic agents.

One aspect of the present invention provides a monoclonal antibody specific for a GPVI polypeptide, peptide, or naturally-occurring variant thereof, that inhibits collagen-induced platelet aggregation at an $IC_{50}$ of less than about 7, 4, 3, 2, 1, 0.6, µg/ml, or any value subsumed within this range. The monoclonal antibody specific for a GPVI polypeptide, peptide, or naturally-occurring variant thereof may also inhibit collagen-induced platelet adhesion at an $IC_{50}$ of less than about 1, 0.5, 0.2, 0.1 µg/ml, or any value subsumed within this range.

Another aspect of the present invention provides a monoclonal antibody specific for a GPVI polypeptide, peptide, or naturally-occurring variant thereof, that specifically binds to a GPVI polypeptide, peptide, or naturally-occurring variant thereof, at a Kd of equal to or lower than $10^{-8}$M. In another embodiment, the anti-GPVI antibodies of the invention specifically bind to a GPVI polypeptide, peptide, or naturally-occurring variant thereof, at a Kd of equal to or lower than $10^{-9}$M.

The monoclonal antibodies of the present invention also inhibit collagen-induced ATP secretion and/or collagen-induced thromboxane $A_2$ formation. The monoclonal antibodies include active antibody fragments. Active antibody fragments may include chemically, enzymatically, or recombinantly produced Fab fragments, $F(ab)_2$ fragments, or peptides comprising at least one complementarity determining region (CDR) specific for a GPVI polypeptide, peptide, or naturally-occurring variant thereof. In an embodiment of the invention, the CDRs comprise any one of the sequences of SEQ ID NOs. 1-24, or a variant thereof, wherein the CDR variant specifically binds a GPVI polypeptide, peptide, or naturally-occurring variant thereof. Exemplary antibodies include OM1, OM2, OM3, and OM4.

The present invention also provides a method for inhibiting platelet aggregation, collagen-induced ATP secretion, collagen-induced thromboxane $A_2$ formation, and/or platelet adhesion, by contacting platelets with a monoclonal antibody specific for a GPVI polypeptide, peptide, or naturally-occurring variant thereof.

The invention further provides a method of producing a monoclonal antibody specific for a GPVI polypeptide, peptide, or naturally-occurring variant thereof. The method comprises immunizing a GPVI-deficient host with a GPVI antigen and obtaining the antibody. A GPVI-deficient host includes, for example, a GPVI heterozygous host and a homozygous GPVI knock-out host. Another aspect of the invention provides monoclonal antibodies specific for a GPVI polypeptide, peptide, or naturally-occurring variant, thereof produced by the method described.

The invention also provides an antithrombotic composition comprising a pharmaceutically effective amount of a GPVI specific monoclonal antibody of the invention. The antithrombotic agent may be used to treat a patient. Thus, an aspect of the invention provides a method of treating a patient who, for example, is in need of treatment for vascular disease.

The invention further provides a method for identifying antithrombotic agents by contacting a GPVI antigen with a GPVI specific monoclonal antibody of the invention and a test compound, and measuring inhibition of the binding of the monoclonal antibody to the GPVI antigen. The GPVI antigen, GPVI specific monoclonal antibody, and the test compound may be added in any order. For example, the GPVI antigen may be contacted with the test compound before contacted with the GPVI specific monoclonal antibody. In another example, the GPVI antigen may be contacted with GPVI specific monoclonal antibody and the test compound simultaneously.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

FIG. 1A shows the wild-type allele of GPVI, the targeting vector used for homologous recombination at exons 2 and 3, and the resulting mutant allele. FIG. 1B shows the size differences of the 5' and 3' fragments derived by cleavage with restriction enzymes in wild-type and mutant genomes.

FIG. 13 illustrates the effects of the OM4 Fab and 7E3 F(ab')$_2$ fragments on bleeding time in rats. FIG. 13A shows the effects on nail bleeding time and FIG. 13B shows the effects on tail bleeding time.

FIG. 15 is a bar graph showing the effect of the OM4 Fab fragment on arterial thrombus formation in rats when administered before (FIG. 15A) and after (FIG. 15B) endothelial injury.

DESCRIPTION OF THE EMBODIMENTS

Figure 1:
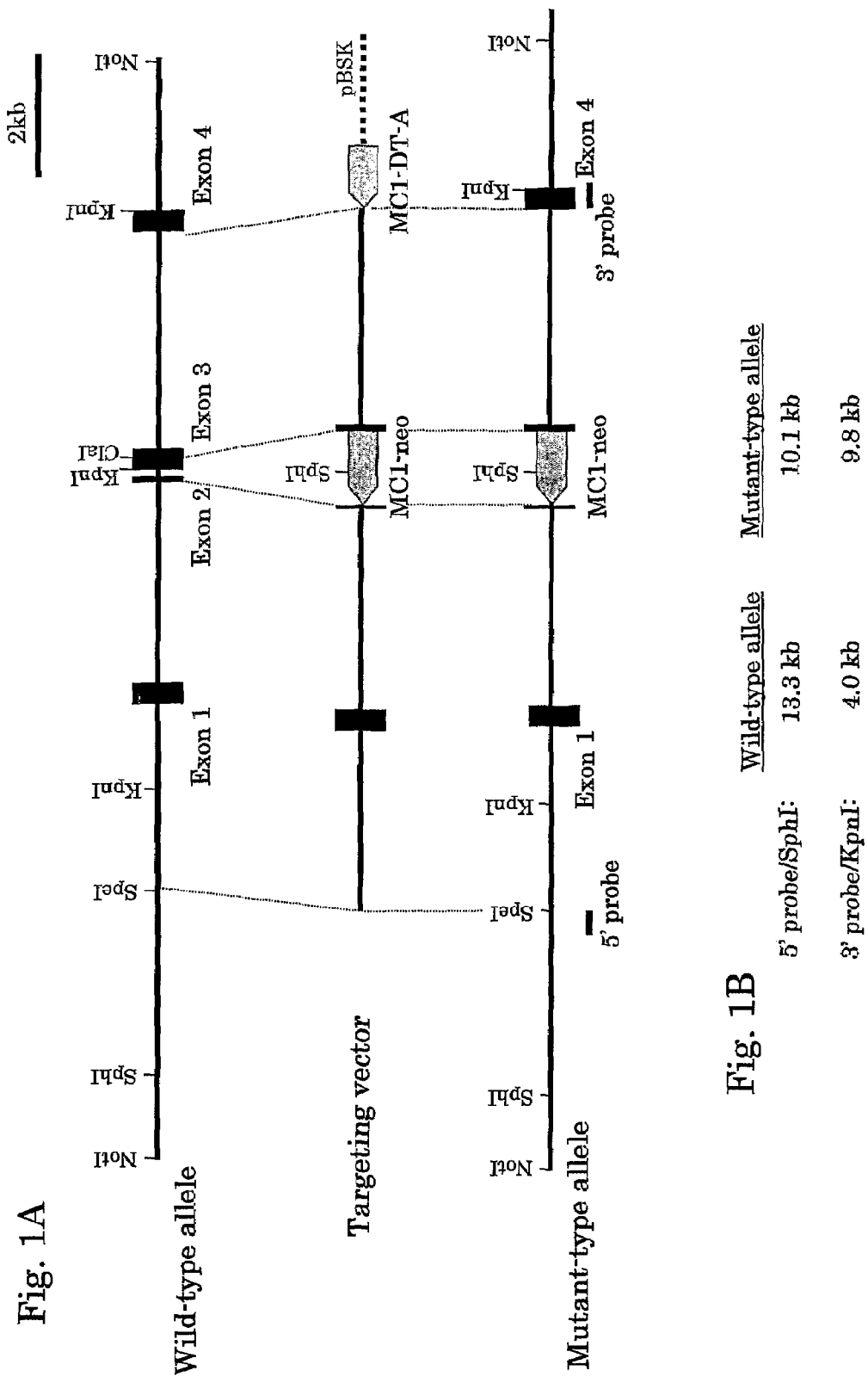
FIG. 1 is a schematic diagram of the generation of GPVI knock-out mice.

This invention describes novel GPVI specific antibodies that are potent inhibitors of collagen-induced platelet responses, including, but not limited to, platelet aggregation, adhesion, collagen-induced ATP release, and thromboxane A$_2$ (TXA$_2$) formation. The invention also describes methods for producing the anti-GPVI antibodies. The anti-GPVI antibodies of the invention may be useful for inhibiting thrombus formation and for treating patients in need of anti-thrombotic treatment.

The term "antibodies" includes monoclonal antibodies. The monoclonal antibodies of the invention include active antibody fragments, such as F(ab')$_2$, and Fab fragments, as well as any recombinantly produced binding partners. Antibodies are defined to be "specifically binding" if they bind a GPVI polypeptide, peptide, or naturally-occurring variant thereof, with a dissociation constant (Kd) equal to or lower than $10^{-7}$M. In an embodiment of the invention, the anti-GPVI antibodies specifically bind to a GPVI polypeptide, peptide, or naturally-occurring variant thereof, at a Kd of equal to or lower than $10^{-8}$M. In another embodiment, the anti-GPVI antibodies of the invention specifically bind to a GPVI polypeptide, peptide, or naturally-occurring variant thereof, at a Kd of equal to or lower than $10^{-9}$M. Affinities of binding partners or antibodies may be readily determined using conventional techniques, for example by measuring the saturation binding isotherms of $^{125}$I-labeled IgG or its fragments, or by homologous displacement of $^{125}$IgG by unlabeled IgG using nonlinear-regression analysis as described by Motulsky, in Analyzing Data with GraphPad Prism (1999), GraphPad Software Inc., San Diego, Calif. Other techniques are known in the art, for example, those described by Scatchard et al., Ann. NY Acad. Sci., 51:660 (1949). GPVI polypeptides, peptides, or naturally-occurring variants thereof, are described in U.S. Publication No. 2003/0186885, and is incorporated herein by reference in its entirety.

Antibodies may be readily generated from a variety of sources, for example, horses, cows, goats, sheep, dogs, chickens, rabbits, mice, hamsters, or rats, using procedures that are well-known in the art. In an embodiment of the invention, the host animals are Armenian hamsters. In another embodiment, the host animals are GPVI-deficient animals. As used herein, "GPVI-deficient" refers to about 50% or greater reduction in endogenous GPVI production in an animal compared to a wild-type animal. The reduction in endogenous GPVI production may be such that GPVI production is completely inhibited. GPVI-deficient animals may be generated by a number of methods known in the art. These may include manipulation of GPVI production at the nucleic acid (DNA or RNA) level in an animal. GPVI-deficient animals may be generated by methods including, but not limited to, knock-out (see, e.g., Galli-Taliadoros et al., J. Immunol. Methods 181: 1-15, 1995; Robbins, Circ. Res. 73:3-9, 1993; Hergueux et al., Transplant Proc. 25:30-32, 1993), knock-in (Colucci-Guyon et al., Cell 79:679-694, 1994; Le Mouellic et al., PNAS 87:4712-4716, 1990; Hanks et al., Science 269:679-682, 1995; Wang et al., Nature 379:823-825, 1996), mutation (Askew et al., Mol. Cell. Biol. 13:4115-4124, 1993; Stacey et al., Mol. Cell. Biol. 14:1009-1016, 1995; Hasty et al, Nature 350:243-246, 1991; Valancius et al, Mol. Cell. Biol. 11:1402-1408, 1991; Wu et al., PNAS 91:2819-2823, 1994; Horie et al., Gene 166:197-204, 1995; Toth et al., Gene 178:161-168, 1996), deletion (You et al., Nature Genet., 15:285-288, 1997; Holdener-Kenny et al., Bioessays 14:831-839, 1992), antisense oligonucleotide technology (Wagner et al., Nature Biotechnol. 14:840-844, 1996; Kitajima et al., Science 258: 1792-1795, 1992; Urban et al., Farmaco. 58:243-58, 2003; Orum et al., Curr Opin Mol Ther. 3:239-43, 2001; Sohail et al., Curr Opin Mol Ther. 2:264-71, 2000; Smith et al., Eur J Pharm Sci. 11:191-8, 2000), interfering RNA (RNAi) technology (Scherr et al., Curr Med. Chem. 10:245-56, 2003; Nishikura, Cell 107:415-418, 2001; Hannon, Nature 4418: 244-251, 2002; U.S. Pat. No. 5,506,559), or by using any other chemicals, naturally-occurring, recombinant, or synthetic peptides, polypeptides, proteins, polysaccharides, small molecules and other compounds designed to reduce or inhibit GPVI production in a host.

Without being bound to theory, hosts that produce none or lower than normal amounts of endogenous GPVI may mount a stronger immune reaction to GPVI than those that make normal levels of GPVI. Thus, antibodies to GPVI that are more effective at inhibiting collagen-induced platelet responses such as platelet aggregation, thrombogenesis, and/or platelet activation at lower doses may be produced compared to those obtained from normal hosts that make GPVI. Methods for producing antibodies in knock-out animals have been described in Pass et al., Scand. J. Immunol. 58:298-305 (2003); Zlot et al., J. Lipid Res. 40:76-84 (1999); Declerck et al., J. Biol. Chem. 270:8397-8400 (1995); and Castrop et al., Immunobiology 193:281-287 (1995).

Hosts may be immunized as described in US Patent Publication No. US 2003/0186885 A1, which is herein incorporated by reference in its entirety. Briefly, hosts may be immunized with "GPVI antigen" which includes, but is not limited to, native GPVI polypeptides, peptides, or naturally-occurring variants thereof, isolated from platelets or other GPVI-expressing cells; recombinant GPVI polypeptides, peptides, or recombinant forms of naturally-occurring variants thereof, expressed from prokaryotic or eukaryotic cells; platelets obtained from various species, including human; cells expressing GPVI polypeptides, peptides, or naturally-occurring variants thereof; nucleic acids encoding GPVI polypeptides, peptides, or naturally-occurring variants thereof; or any combination thereof.

Purified GPVI polypeptides, or a peptide based on the amino acid sequence of GPVI polypeptides conjugated to an adjuvant or carrier, are typically administered to the host animal intraperitoneally. The immunogenicity of GPVI polypeptides may be enhanced through the use of an adjuvant, for example, Freund's complete or incomplete adjuvant. Following booster immunizations, small samples of serum are collected and tested for reactivity to GPVI polypeptides. Examples of various assays useful for such determination include those described in: Antibodies: A Laboratory Manual, Harlow and Lane (eds.), Cold Spring Harbor Laboratory Press, 1988; as well as procedures such as countercurrent immuno-electrophoresis (CIEP), radioimmunoassay, radioimmunoprecipitation (RIP), enzyme-linked immunosorbent assays (ELISA), dot blot assays, and sandwich assays and FACS. See U.S. Pat. Nos. 4,376,110 and 4,486,530.

Monoclonal antibodies can be readily prepared using well-known procedures, see for example, the procedures described in U.S. Pat. No. RE 32,011, U.S. Pat. Nos. 4,902,614, 4,543,439, and 4,411,993; Monoclonal Antibodies, Hybridomas: A New Dimension in Biological Analyses, Plenum Press, Kennett, McKearn, and Bechtol (eds.), 1980. Briefly, the host animals are injected intraperitoneally at about 1 week intervals with a GPVI antigen, optionally in the presence of adjuvant. Immunizations are carried out until desired titer of antibody is achieved.

Mouse sera are then assayed for antibody titer by FACS analysis using GPVI-FcR$\gamma$ chain transfected CHO cells, or any other method known in the art. The selected mice are given a booster dose of the GPVI antigen. Three days later, the mice are sacrificed and their spleen cells are fused with commercially available myeloma cells, P3U1 (ATCC), following established protocols. Myeloma cells are washed several times in serum-free media and fused to mouse spleen cells. The fusing agent is 50% PEG (Roche). Fusion is plated out into eight 96-well flat bottom plates (Corning) containing HAT supplemented DMEM media and allowed to grow for 1-2 weeks. Supernatants from resultant hybridomas are collected and analyzed for the presence of anti-GPVI antibodies by performing FACS analysis using CHO cells expressing GPVI and FcR$\gamma$-chain. FACS analysis is also performed using wild-type CHO cells to eliminate clones producing antibodies against CHO cell antigens. Positive clones can be grown in bulk culture and supernatants are subsequently purified over a Protein A or G Sepharose column (Pharmacia). It is understood that many techniques could be used to generate antibodies against GPVI polypeptides and peptides and that this embodiment in no way limits the scope of the invention.

The monoclonal antibodies of the invention may be produced using alternative techniques, such as those described by Alting-Mees et al., "Monoclonal Antibody Expression Libraries: A Rapid Alternative to Hybridomas", in Strategies in Molecular Biology 3:1-9 (1990), which is incorporated herein by reference. Similarly, binding partners constructed, for example, using recombinant DNA techniques to incorporate the variable regions of a gene that encodes a specific binding antibody, are included in the monoclonal antibodies of the invention. Such a technique is described in Larrick et al., Biotechnology, 7:394 (1989).

Other types of antibodies may be produced in conjunction with the state of knowledge in the art. For example, antiidiotype antibodies may be obtained by immunizing a host with an antigen comprising the antigen binding site of a purified monoclonal anti-GPVI antibody, and testing the resultant sera or monoclonal supernatant for activity as described in Knight et al., Mol. Immunol. 32:1271-81 (1995). In an embodiment of the invention, the antiidiotype antibodies may be obtained by immunizing a host with a peptide comprising a complementarity determining region (CDR) of an anti-GPVI antibody of the invention. The antiidiotype antibodies of the invention include active antiidiotype antibody fragments, which refer to chemically, enzymatically, or recombinantly produced fragments of an antiidiotype antibody, including, Fab, F(ab)$_2$, or peptides comprising at least one complementarity determining region (CDR) that bind specifically to an anti-GPVI antibody. In addition, the invention comprises biosynthetic GPVI antibody binding sites, as described by Huston et al., Proc. Natl. Acad. Sci. USA 85:5879 (1988); single-domain antibodies comprising isolated heavy chain variable domains, as described by Ward et al., Nature 341:544 (1989); and antibodies that have been engineered to contain elements of human antibodies that are capable of specifically binding GPVI polypeptides. Anti-GPVI antibodies may also be generated using the phage display technology as described in Ventor et al., Ann Rev. Immunol. 12:43355 (1994) and the references cited therein, all of which are incorporated herein by reference.

The antibodies of the invention also include active antibody fragments, which refer to chemically, enzymatically, or recombinantly produced fragments of an antibody, including, Fab, F(ab)$_2$, or peptides comprising at least one complementarity determining region (CDR) that bind specifically to a GPVI polypeptide, peptide, or a naturally-occurring variant thereof. A common enzymatic method utilizing pepsin or papain removes the Fc antibody domain to produce bivalent F(ab)$_2$ and monovalent Fab fragments. These procedures are basically described in Gorini et al., J. Immunol. 103:1132 (1969); Handbook of Experimental Immunology Vol 1: DM Wier (ed), Blackwell Alden Press, Oxford, UK, 1997; and Antibodies: A Laboratory Manual, Harlow and Lane (eds.), Cold Spring Harbor Laboratory Press, 1988; and U.S. Pat. No. 4,470,925 (Auditore-Hargreaves), all of which are incorporated herein by reference.

Intact GPVI-specific antibodies, and antibody fragments, such as Fab and F(ab)$_2$ fragments, may be covalently coupled to drugs or carrier molecules. In addition, the GPVI-specific antibodies of the invention may be cross-linked, directly, or through a suitable carrier molecule, to form multivalent complexes. In one embodiment, F(ab)$_2$ fragments are metabolically stabilized by covalent cross linking as described in Reno et al. (U.S. Pat. No. 5,506,342) (incorporated herein by reference)

Monoclonal antibodies specific for a GPVI polypeptide, peptide, or a naturally-occurring variant thereof, may be tested for their ability to block platelet activation by ligand (collagen)-dependent binding. Monoclonal antibodies which block platelet functions may be useful antithrombotic agents.

The antibodies of the present invention may also be humanized. Human and humanized antibodies are thus preferred for clinical use. See, for example, LoBugio et al., Proc. Natl. Acad. Sci. USA 86:4220-24 (1989); Meredith et al., J. Nucl. Med. 33, 23-29 (1992); Salah et al., Hum. Antibod. Hybridomas 3:19-24 (1992); Knight et al., Mol. Immunol. 32:1271-81 (1995); and Lockwood et al., Q. J. Med. 89:903-12, (1996).

Development of fully human antibodies generally require a suitable source of human immune B lymphocytes. One method for generating human antibodies involves the immunization and expansion of B lymphocytes with suitable specificities from pools of naïve B cells obtained from non-immunized individuals that were placed in in vitro culture. Ohlin and Borrebaeck, in Methods of Immunological Analysis, vol. II, Masseyeff et al. (eds), VCH Verlagsgesellschaft mbH, Weinheim, p. 298-325 (1992); Borrebaeck and Ohlin, in Protocols in Cell and Tissue Culture, Doyle et al. (eds), J. Wiley & Sons Ltd., Chichester 25E:1.1-7 (1993). Human antibodies against HIV-1 glycoproteins have been developed by this method. Ohlin et al., Immunology 68:325-331 (1989); Ohlin et al., Clin. Exp. Immunol. 89:290-295 (1992); Duenas et al., Immunology 89:1-7 (1996). More recently, in vivo technologies have been developed that utilize animals either engrafted with human immune cells or those that have been introduced with the entire human immunoglobulin loci. Ilan et al., Curr. Opin. Mol. Ther. 4:102-109 (2002); Ishida et al., Cloning Stem Cells 4:91-102 (2002). Fully human antibodies have been produced upon immunization of these animals with various human antigens.

Humanized antibodies may be generated by replacing most, or all, of the structural portions of a monoclonal antibody with corresponding human antibody sequences. Consequently, a hybrid molecule is generated in which only the antigen-specific variable, or complementarity determining region (CDR) is composed of non-human sequence. Various strategies for designing humanized antibodies are reviewed in Winter and Milstein, Nature 349:293-99 (1991); Harris, BCSTBS5 23(4):1035-38 (1995); Morrison and Schlom, in Important Advances in Oncology, J. B. Lippincott Co. (1990); L. Presta, "Humanized Monoclonal Antibodies," in Annual Reports in Medicinal Chemistry, Academic Press, (1994); and A. Lewis and J. Crowe, "Generation of Humanized Monoclonal Antibodies by 'Best Fit' Framework Selection and Recombinant Polymerase Chain Reaction" in Generation of Antibodies by Cell and Gene Immortalization. Year Immunol. 1993, vol 7, pp 110-118, (C. Terhorst, F. Malvasi, and A. Albertini (eds.) Basel, Karger, each of which is incorporated herein by reference.

Antibodies specific for a GPVI polypeptide, peptide, or naturally-occurring variant thereof, may also be humanized by selecting and purifying anti-GPVI antibodies by Ig-specific adsorption, such as Protein A chromatography, or by affinity chromatography using immobilized GPVI peptides. The heavy and light chains may be dissociated by standard means, and the individual chains purified. A partial amino acid sequence of the individual chains may be determined and degenerate oligonucleotides may be generated for each chain according to the method of Lathe et al., J. Mol. Biol. 183:1-12 (1985). The DNA encoding these antibody chains may then be cloned and sequenced from the anti-GPVI antibody-producing cell by PCR or other standard methods.

The antibody DNA and amino acid sequence may be analyzed and compared with known sequences of human heavy and light chains. Based on the sequence comparisons, the GPVI-specific antibody chains may be humanized by replacing portions of the non-human DNA with human sequences, thus forming a chimeric antibody with specificity to GPVI. In one embodiment, the GPVI-specific antibody is humanized with human J1 and K constant regions using the expression vectors described by Sun et al., Proc. Natl. Acad. Sci. USA 84:214-218 (1987). Methods for the preparation of nonhuman-human hybrids are well known in the art and described in detail in, for example, Knight et al., Mol. Immunol. 32:1271-81 (1995); U.S. Pat. No. 5,705,154 (Dalie et al.); 5,693,322 (Creekmore et al.); U.S. Pat No. 5,677,180 (Robinson et al.); U.S. Pat. No. 5,646,253 (Wallace et al.); U.S. Pat. No. 5,585,097 (Bolt et al.); U.S. Pat. No. 5,631,349 (Diamantstein et al.); and U.S. Pat. No. 5,580,774 (Beavers et al.) (each of which is incorporated herein by reference). To maximize the production of high affinity chimeric antibodies, the methods of Queen et al., (U.S. Pat. No. 5,585,089) and Queen et al., Proc. Nat. Acad. Sci. USA, 86:10029-33 (1989), may be employed.

Humanized antibodies may also be generated using the phage display approach as taught in Rader et al., Proc. Nat. Acad. Sci. USA, 95:8910-8915 (1998) and Steinberger et al., J. Biol. Chem. 275:36073-36078 (2000) and as exemplified by Son et al., J Immunol Methods. 286:187-201 (2004), Lee et al., J Immunother. 27:201-210 (2004), and by others skilled in the art.

The part of the antibody molecule that binds to an antigen is comprised of only a small number of amino acids in the variable (V) regions of the heavy (VH) and light (VL) chains. These amino acids are brought into close proximity by folding of the V regions. Comparisons of the amino acid sequences of the variable regions of IgG show that most of the variability resides in three regions called the complementarity determining regions (CDRs). Each chain (H and L) contains three CDRs. Antibodies with different specificities have different CDR's while antibodies of the exact same specificity generally have identical or highly conserved CDR's. The present invention encompasses monoclonal antibodies or peptides comprising at least one complementarity determining region (CDR), or a variant thereof, of the GPVI antibodies of the invention. The invention encompasses monoclonal antibodies or peptides comprising at least one of the amino acid sequences of SEQ ID NOs. 1-24, or variants thereof.

A "variant" of an antibody or a peptide comprising a CDR herein refers to an antibody or peptide comprising an amino acid sequence substantially identical to SEQ ID NOs. 1-24, but which has an amino acid sequence different from that of SEQ ID NOs. 1-24 because of one or more deletions, insertions or substitutions. The variant also retains at least 70, 80, 90 or 100% of its binding affinity to a GPVI polypeptide, peptide, or naturally-occurring variant thereof, compared with an antibody or peptide comprising its corresponding CDR. Binding affinities may be determined according to any method known in the art, for example, as taught by Fujimura et al., Thromb. Haemost. 87:728-734 (2002) and as exemplified in Example 4 below. A variant comprises a CDR that is preferably at least 60%, 65%, 70%, 80%, 85%, or 90% identical to SEQ ID NOs. 1-24. The percent identity can be determined, for example, by comparing sequence information using the GAP computer program, version 6.0 described by Devereux et al. (Nucl. Acids Res. 12:387, 1984) and available from the University of Wisconsin Genetics Computer Group (UWGCG). The GAP program utilizes the alignment method of Needleman and Wunsch (J. Mol. Biol. 48:443, 1970), as revised by Smith and Waterman (Adv. Appl. Math 2:482, 1981). The preferred default parameters for the GAP program include: (1) a unary comparison matrix (containing a value of 1 for identities and 0 for non-identities) for nucleotides, and the weighted comparison matrix of Gribskov and Burgess (Nucl. Acids Res. 14:6745, 1986), as described by Schwartz and Dayhoff, eds., Atlas of Protein Sequence and Structure, National Biomedical Research Foundation, pp. 353-358, 1979; (2) a penalty of 3.0 for each gap and an additional 0.10 penalty for each symbol in each gap; and (3) no penalty for end gaps.

Variants may comprise conservatively substituted sequences. Conservative substitution refers to replacement of a given amino acid residue with a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known.

Candidate anti-GPVI antibodies may be screened for effects on platelet adhesion and activation using various assays known in the art. These include, for example, the platelet adhesion inhibitor assay described in U.S. Pat. No. 5,686,571; a modified constant flow assay of Diaz-Ricart et al. (Blood 82:491-496, 1993) that allows the use of a smaller volume of blood and less antibody, as described in Brown and Larson (BMC Immunology 2:9-15, 2001); the plate assay described in Matsuno et al. (British J. Haematology 92:960-967, 1996) and in Nakamura et al. (J. Biol. Chem. 273(8): 4338-44, 1998) (the "Nakamura procedure"), (each of which is specifically incorporated herein by reference). In each case, candidate GPVI agonists or antagonists may be pre- or co-incubated with the reaction components in the presence or absence of $Mg^{2+}$. Incubation in the absence of $Mg^{2+}$ blocks the function of GPIa/IIa such that the remaining collagen-dependent activity is primarily mediated by the GPVI receptor.

A modified Nakamura procedure may be used to measure platelet adhesion to immobilized acid insoluble fibrillar collagen under static conditions. The modified Nakamura assay is described briefly below. The major modification to the original assay includes the replacement of $^{51}$Cr-labeled platelets with unlabeled platelets and the measurement of adhesion by quantification of LDH activity released by adherent platelets using a commercially available kit. One of skill in the art recognizes how to make other modifications to the assay conditions in view of the particular anti-GPVI antibody tested.

Adhesion Assay—Microtiter wells are coated with type I acid-insoluble equine tendon fibrillar collagen. Platelets at a concentration of $4 \times 10^8$/ml are suspended in Tyrode-HEPES buffer or in Tyrode-HEPES buffer supplemented with $Mg^{2+}$ (1 mM), and adhesion assays are carried out as described previously (Tandon et al., Br. J. Haematol. 89:124-30, 1995). Briefly, the platelets are incubated with a sample such as an antibody solution for 30 minutes at room temperature prior to their addition to the collagen-coated wells. Adhesion is carried out for 60 minutes at room temperature in the presence and absence of $Mg^{2+}$. Unattached platelets are removed by repeated washing of the wells and the adhered platelets are solubilized in Triton X-100. A commercially available LDH measuring kit (CytoTox 96, Promega, Madison, Wis., USA) based on a calorimetric assay is used to measure released LDH activity.

Assay for ATP Release and Thromboxane $A_2$ ($TXA_2$) generation—Collagen-induced ATP release is measured in a dual channel lumiaggregometer (Model 650CA—Chronolog Corporation Havertown Pa., USA). Briefly, platelet rich plasma (platelet count adjusted to $3 \times 10^8$/ml with platelet poor plasma) is mixed with luciferase-luciferin reagent (Chronolog Corporation). Platelets are incubated at 37° C. for 5 minutes in the presence and absence of a test antibody solution, e.g. Fab fragments, prior to challenge with collagen. Aggregation and ATP release are measured simultaneously. At desired times, the reaction is stopped by addition of a cocktail of inhibitors that inhibit synthesis of $TXA_2$. The supernatant of platelet suspension is transferred to a small tube and frozen at −20° C. until measured for collagen-induced $TXA_2$ formation. $TXA_2$ is measured as $TXB_2$, a stable metabolite of $TXA_2$.

Platelet Aggregation Assay—A simple assay for detecting or determining antithrombotic activity is provided by the platelet aggregation assay described in Sun et al., J Cardiovascular Pharmcol. 40:557-585 (2002). Anti-GPVI antibodies, e.g., intact IgG, F(ab')$_2$, or Fab fragments, or control buffer (0.15 M NaCl, 0.01 M Tris.HCl, pH 7.4), is added to a cuvette containing platelet-rich plasma (200 µl). The mixture is incubated for 3 to 5 minutes at 37° C. in the heating module of an aggregometer prior to inducing aggregation with collagen. The cuvette is placed in a four channel aggregometer (AG10 Kowa, Japan), which measures the kinetics of particle formation by laser scattering and aggregation by changes in light transmission. Aggregation is initiated with 0.5-4 µg/ml of collagen. The optimal concentrations or collagen are those that give at least 70% change in light transmission and are determined for each experiment. Aggregation is monitored for at least 8-10 minutes after the addition of collagen.

In-vitro Assay—The GPVI specific antibodies or antibody fragments may be further assayed using the systems developed by Diaz-Ricart and co-workers (Arteriosclerosis, Thromb. Vasc. Biol. 16:883-888, 1996). This assay determines the effect of GPVI antibodies on platelets under flow conditions using de-endothelialized rabbit aorta and human endothelial cell matrices.

In vivo Assay—The in vivo activity of GPVI antibodies or antibody fragments may be assayed using standard models of platelet function as described in Coller and Scudder, Blood 66:1456-59 (1985); Coller et al., Blood 68:783-86 (1986); Coller et al., Circulation 80:1766-74 (1989); Coller et al., Ann. Intern. Med. 109:635-38 (1988); Gold et al., Circulation 77, 670-77 (1988); and Mickelson et al., J. Molec. Cell Cardiol. 21:393-405 (1989).

The above tests demonstrate that the GPVI specific antibodies of the invention are more potent than those previously reported by others. Specifically, the GPVI specific antibodies of the invention inhibit collagen-induced platelet aggregation at a lower $IC_{50}$ than antibodies in the art. The term "$IC_{50}$" is known in the art as the concentration at which 50% inhibition is observed and is any positive value greater than zero. The $IC_{50}$ for inducing inhibition of collagen-induced platelet aggregation was determined using a concentration of collagen that induced 70-90% platelet aggregation within 5 minutes of its contact with platelets. The terms "inhibition" or "inhibit" refers to a decrease or cessation of any phenotypic characteristic or to the decrease or cessation in the incidence, degree, or likelihood of that characteristic. In the context of platelet aggregation, "inhibition" refers to a measurable decrease or cessation in the aggregation of platelets. Such inhibition may be detected by the test described above, or by any other method known in the art. Similarly, "inhibition" in the context of platelet adhesion refers to a measurable decrease or cessation in the adhesion of platelets to a surface and such inhibition may be detected by the test described above, or by any other method known in the art.

The GPVI specific antibodies of the invention inhibit collagen-induced platelet aggregation at an $IC_{50}$ of less than about 7, 4, 3, 2, 1, 0.6 µg/ml, or any value subsumed within this range. The GPVI specific antibodies of the invention also inhibit collagen-induced platelet adhesion at an $IC_{50}$ of less than or equal to about 1, 0.5, 0.2, 0.1 µg/ml, or any value subsumed within this range. The GPVI specific antibodies of the invention also inhibit collagen-induced ATP secretion and/or collagen-induced thromboxane $A_2$ formation. The GPVI specific antibodies of the invention include active antibody fragments. Active antibody fragments include chemically, enzymatically, or recombinantly produced Fab fragments, F(ab)$_2$ fragments, and peptides comprising at least one complementarity determining region (CDR) specific for a GPVI polypeptide, peptide, or naturally-occurring variant thereof.

The GPVI specific antibodies of the invention may be formulated into pharmaceutical compositions according to known methods. The pharmaceutical composition of the invention comprises at least one GPVI specific antibody and include, but are not limited to, intact monoclonal antibodies; Fab fragments; F(ab)$_2$ fragments; and peptides comprising at least one CDR sequence, or variant thereof. The GPVI specific antibody may be combined with other known active materials.

Compositions of the invention include at least one GPVI specific antibody admixed with pharmaceutically acceptable excipients, including, but not limited to, diluents (e.g., Tris-HCl, acetate, phosphate, water), preservatives (e.g., Thimerosal, benzyl alcohol, parabens), emulsifiers, salts, polymers, buffers, solubilizers, adjuvants and/or carriers. Suitable excipients and their formulations are described in Remington: The Science and Practice of Pharmacy, 20th ed, Mack Publishing Co. (2000). In addition, such compositions may contain GPVI specific antibodies complexed with polyethylene glycol (PEG), metal ions, incorporated into polymeric compounds such as polyacetic acid, polyglycolic acid, hydrogels, etc., or incorporated into liposomes, microemulsions, micelles, unilamellar, multilamellar, or colamellar vesicles, erythrocyte ghosts or spheroblasts.

The instant invention also comprises methods of inhibiting thrombosis, for example, by inhibiting platelet aggregation or platelet adhesion, comprising contacting activated or resting platelets with antibodies directed against GPVI. "Inhibiting thrombosis" refers to a decrease or cessation of a thrombotic event or to the decrease in the incidence, degree, or likelihood of thrombotic events in a patient, patient population, or in vitro test systems. The invention also relates to the treatment of a patient, hereby defined as any person or non-human animal in need of anti-thrombotic treatment to reduce the incidence, likelihood, or degree of thrombosis, or platelet aggregation, or platelet activation, or to any subject for whom treatment may be beneficial for the treatment of vascular disease, including humans and non-human animals. Such non-human animals to be treated include all domesticated and feral vertebrates including, but not limited to: mice, rats, rabbits, fish, birds, hamsters, dogs, cats, swine, sheep, horses, cattle, and non-human primates.

The treatment of a patient comprises the administration of a pharmaceutically effective amount of an anti-GPVI antibody-containing composition of the invention. One of ordinary skill in the art may empirically determine the optimum dosage and dosage schedule for administering these compositions. Nevertheless, a pharmaceutically effective amount is that amount which provides a measurable anti-thrombotic effect, for example, a reduction in the incidence, degree, or likelihood of thrombosis, platelet aggregation, or platelet activation as measured in vivo or in vitro, or provides a measurable decrease in the likelihood, incidence, or degree of vascular disease, clot or emboli formation, or ischemic events in a patient.

A pharmaceutically effective amount may be administered as a single dose or as multiple doses over the course of treatment. A kit within the scope of the invention comprises encompasses a container containing one or more doses of a pharmaceutically effective amount of an anti-GPVI antibody-containing composition of the invention. Such kits encompass anti-GPVI antibodies alone, admixed or suspended with a suitable pharmaceutically acceptable diluent and/or other excipient, or formulated to be admixed or suspended in a suitably acceptable diluent and/or other excipient prior to administration.

The compositions of the invention may be administered by any method familiar to those of ordinary skill in the art, for example, intravenous administration by bolus injection, continuous, or intermittent infusion. In alternative embodiments, the compositions may be administered intraperitoneally, intracorporeally, intra-articularly, intraventricularly, intrathecally, intramuscularly, subcutaneously, topically, tonsillarly, mucosally, intranasally, transdermally, intravaginally, orally, or by inhalation.

The GPVI specific antibodies of the invention may also be used to screen for compounds that may be useful as anti-thrombotic agents. The screening method comprises contacting a GPVI antigen with a test compound and a GPVI specific antibody and measuring the inhibition of binding of the GPVI specific antibody to the GPVI polypeptide, peptide, or a naturally-occurring variant thereof. The GPVI antigen, GPVI specific antibody, and the test compound may be added in any order. For example, the GPVI antigen may be contacted with the test compound before contacted with the GPVI specific monoclonal antibody. In another example, the GPVI antigen may be contacted with GPVI specific monoclonal antibody and the test compound simultaneously.

Inhibition of binding suggests that the test compound competes for, or otherwise interferes with, the same binding site on GPVI as the GPVI specific antibody. "GPVI antigen" in the context of screening for anti-thrombotic agents, refers to, but is not limited to, native GPVI polypeptides, peptides, or naturally-occurring variants thereof, isolated from platelets or other GPVI-expressing cells; recombinant GPVI polypeptides, peptides, or naturally-occurring variants thereof, expressed from prokaryotic or eukaryotic cells; or cells expressing GPVI polypeptides, peptides, or naturally-occurring variants thereof. A test compound may be any chemical, protein, peptide, polypeptide, or nucleic acid (DNA or RNA). The test compound may be naturally-occurring or may be synthesized by methods known in the art. The screening method of the invention may employ high-throughput screening (HTS) methods. High-throughput screening methods are reviewed in Khandurina et al., Curr Opin Chem Biol. 6:359-66 (2002); Kumble, Anal Bioanal Chem. 377:812-819 (2003); and Bleicher et al., Nature Rev Drug Disc 2:369-378 (2003).

A compound identified as inhibiting the binding of a GPVI specific antibody, or an antibody fragment thereof, to a GPVI antigen, may be further tested for its effect on platelet functions by any of the methods disclosed herein, or by other methods known in the art. These platelet functions include collagen-induced platelet aggregation, collagen-induced platelet adhesion, collagen-induced ATP secretion, and collagen-induced thromboxane $A_2$ formation.

The present invention is illustrated by the following Examples, which are not intended to be limiting in any way.

EXAMPLE 1

Preparation of Monoclonal GPVI Antibodies

Normal mice (Balb/c, female), Armenian hamsters (male) and GPVI knock-out mice (produced at Otsuka GEN institute) were immunized to produce monoclonal antibodies as described below.

GPVI knockout mice were generated as previously described (Mori et. al. Neurosci. Res. 43: 251-7, 2002). The targeting vector was constructed by replacing a genomic fragment of the GPVI gene (Ezumi Y. et al., Biochem Biophys Res Comm 277:27-36, 2000) from 129/Sv mouse genomic λ clones containing the last 5 bases of exon 2 to the first half of exon 3 (ClaIsite) with the pMC1-neo-polyA (Stratagene) cassette as shown in FIG. 1A. The linearized construct was electroporated into AB2.2 ES cells derived from 129/Sv mouse (Lexicon Genetics Inc., The Woodlands, Tex.) and the cells were selected in G-418. G-418-resistant ES cell clones were screened for successful homologous recombination at exons 2 and 3 by probing SphI- or KpnI-digested genomic DNAs with 5' or 3' external probes, respectively (FIG. 1B; Southern blotting data not shown). Chimeric mice derived from the homologous recombinant ES cells were mated with C57BU6J mice to obtain heterozygous mutants (F1). Homozygous mutants (F2) were derived by mating the obtained heterozygous mutants and confirmed by Southern blotting. Mice were genotyped by polymerase chain reaction (PCR) using genomic DNA extracted from tail snips. No abnormalities in birth rate, birth weight, growth and development, Mendelian distribution, or bleeding disorders were observed in the homozygous mutants. Background-matched wild-type and heterozygous mice were used as controls. Armenian hamsters were obtained from Cytogen Research and Development Inc. Boston, Mass. All animals were kept and bred according to the Institutional Animal Care and Use Committee (IACUC) protocol at Otsuka Maryland Medicinal Laboratories.

Normal mice were immunized with plasmid containing GPVI cDNA ("p-target"), CHO cell line expressing GPVI-FcRγ chain ("CGP6", wherein transfection was performed using Lipofectamine™ 2000 from Invitrogen), GPVI purified from GPVI-FcRγ expressing CHO cells ("PGP6"), native GPVI purified from human platelets ("nGP6") and recombinant partial GPVI (lacking the first Ig domain) expressed in E. coli ("PAGP6"). Native GPVI from human platelets and PGP6 from GPVI-FcRγ transfected cells were purified by combining the lectin affinity, ion-exchange chromatography, and convulxin-affinity methods described in U.S. Publication No. 2003/0186885.

CHO cells stably expressing GPVI and FcRγ ("CGP6") were established by co-transfection of pTarget vector (Promega) containing full-length human GPVI cDNA ("p-target") and pcDNA3.1 (+)zeocin vector (Invitrogen) containing full-length FcRγ cDNA using Lipofectamine 2000 (Invitrogen). Cells expressing both receptors were selected in medium supplemented with G418 and zeocin. Expression of GPVI was detected by FACS analysis with the Epic Altra FACS analyzer (Beckman Coulter) using a polyclonal human anti-GPVI antibody (Dr. Okuma's serum described earlier) or a FITC-labeled convulxin. Detection of FcRγ expression was performed by immunoblotting using commercially available anti-FcRγ polyclonal antibody (Upstate Biotechnology).

Recombinant partial GPVI was prepared by inserting into the pET21 vector (Novagen) a cDNA encoding a GPVI polypeptide lacking the entire first Ig domain of human GPVI. This partial protein was expressed in E. Coli strain BL21 (DE3). Expressed protein ("PAGP6") was purified from the inclusion bodies as described by the manufacturer.

Armenian hamsters were immunized with CGP6 and human platelets. GPVI knock-out mice were also immunized with CGP6 and human platelets.

Immunogens except p-target were injected intraperitoneally. P-target was injected intradermally. Recombinant or purified proteins were injected as an emulsion with adjuvant (Titermax Gold, Cytrx Corporation). Some of the antigens were immunized with mouse IL-6 (500 U/injection) to boost the immune system. Animals were immunized until a serum titer between 10-50,000 was obtained.

Monoclonal antibodies were produced by conventional hybridoma technology. As a fusion partner, P3U1 cells were used. For screening for positive hybridoma clones, FACS analysis was performed in the Epic Altra FACS analyzer by Beckman Coulter using GPVI-FcRγ expressing CHO cells. For CGP6-immunized animals, FACS analysis was performed with both GPVI-FcRγ-transfected and non-transfected wild-type CHO cells to distinguish clones that produced non-GPVI antibodies e.g. antibodies to CHO cell-related antigens.

Hybridoma cells producing anti-GPVI antibodies were then grown in medium containing 10% fetal calf serum (Invitrogen Corporation, Calif.) (which contained negligible amounts of bovine IgG <1 μg/ml serum). IgG was purified from the cell-free culture supernatant by protein G-Sepharose (Amersham Biosciences, N.J.) or Protein A-Sepharose (Amersham Biosciences, N.J.) affinity chromatography on a Waters 650 system (Waters Corporation, Mass.). Mouse IgG was purified by affinity chromatography on Protein G-Sepharose. Hamster IgG was purified on Protein A-Sepharose. Protein G-bound IgG was eluted from the affinity matrix with low pH glycine (pH 2.75), collected into basic solution to neutralize the acid, and dialyzed in saline for use in functional assays. Protein—A bound hamster IgG was eluted with a pH gradient 7.5-3.0. Antibody was eluted at pH 4.5. In most cases, antibody was >90% pure when analyzed in Agilent 2100 Bioanalyzer (Agilent Technology).

Bivalent F(ab')$_2$ fragments were prepared from intact IgG by papain digestion using standard methods. A solution of IgG (5 mg/ml) was made in 100 mM citric acid, pH 6.5 and 5.0 mM EDTA and digested for 15 hrs at 37° C. with pre-activated papain (cysteine free) at an enzyme to IgG ratio of 1:50 (wt/wt). The reaction was quenched with freshly prepared iodoacetamide and F(ab')$_2$ fragments were separated from undigested IgG and Fc by ion exchange chromatography on a MonoQ column (Amersham Biosciences, N.J.). Fractions containing F(ab')$_2$ were pooled, concentrated and reduced/alkylated to obtain monovalent Fab fragments according to the method of Parham et al., J. Immunol. Meth. 53: 133-173 (1982). Finally, Fab fragments were purified to homogeneity by size exclusion chromatography on Superdex 75 (Amersham Biosciences, N.J.). Direct conversion of IgG into monovalent Fabs by papain in the presence of cysteine was avoided because in a few cases, papain over-digested the IgG, giving rise to unstable and smaller-sized Fab fragments.

Initially, wild-type Balb/c mice were immunized as described above with immunogens including purified GPVI from human platelets ("nGP6"), plasmid containing GPVI cDNA ("p-target"), and CHO cells expressing the GPVI-FcRγ chain complex ("CGP6"). See Table 1. After screening more than 8500 clones, 3 clones with significant but moderate affinity to GPVI were identified (two from CGP6 and one from PGP6). Surprisingly, more than 5500 clones arising from immunizations with p-target, nGPVI, and PAGP6 did not yield a single GPVI-positive clone with biological activity. In an attempt to obtain antibodies with enhanced affinity and biological activity, a different species of animals was immunized. Armenian hamsters were immunized with CGP6 because this immunogen produced two positive clones in wild-type mice. Because human platelets express native GPVI on their surface, washed human platelets were also used as immunogens. Seven GPVI-positive clones were obtained from the CGP6 immunizations and one clone from human platelet immunization. See Table 2.

TABLE 1

Immunization of Wild-type Mice

| Immunogen | # of clones screened | # of positive clones |
|---|---|---|
| p-target | 1192 | 0 |
| CGP6 | 1953 | 2 |
| PGP6 | 1064 | 1 |
| nGP6 | 3797 | 0 |
| PAGP6 | 764 | 0 |
| Total | 8770 | 3 |

TABLE 2

Immunization of Hamsters

| Immunogen | # of clones screened | # of positive clones |
|---|---|---|
| CGP6 | 1547 | 7 |
| human platelets | 1414 | 1 (OM3) |
| Total | 2961 | 8 |

GPVI knock-out (GPVI-KO) mice were then used as hosts for immunization. The GPVI-KO mice lack GPVI and do not respond to high doses of collagen and to convulxin (a GPVI specific agonist). Therefore, it was theorized that injected GPVI may be more antigenic in GPVI-deficient mice and may therefore produce GPVI antibodies having high affinity for GPVI-peptide. The results of immunization of GPVI-KO mice are shown in Table 3. Immunization of GPVI-KO mice with washed human platelet suspensions did not produce any positive clones. However, eight clones were obtained from the immunization of GPVI-KO mice with CGP6, which had high affinity to GPVI as judged by the large rightward shift in fluorescence intensity in the FACS analysis.

TABLE 3

Immunization of GPVI Knock-Out Mice

| Immunogen | # of clones screened | # of positive clones |
|---|---|---|
| CGP6 | 3889 | 8 (including OM1, OM2 and OM4) |
| human platelets | 397 | 0 |
| Total | 4286 | 8 |

IgG immunoglobulins were then obtained from the GPVI-positive clones: 3 clones from wild type mice, 8 clones from hamster fusions, and eight clones from GPVI-KO mice fusions. IgG was purified by affinity chromatography using either Protein G (wild-type and GPVI-KO mice) or Protein A (hamsters), as described above. Purified antibodies from all clones induced full platelet aggregation at relatively small concentrations of IgG at 0.1-7 µg/ml (17 clones) and 10-30 µg/ml (2 clones), suggesting that these antibodies cross-linked GPVI and FcR IIA, or cross-linked GPVI molecules. To exclude the possibility of GPVI-FcRIIA cross linking, F(ab')2 fragments were prepared. In preliminary studies, F(ab')$_2$ fragments prepared from two antibodies activated human platelets, although several fold higher concentrations were needed compared to intact IgGs. This confirmed that GPVI cross linking by the bivalent antibodies may be the cause of the observed platelet activation. In order to avoid GPVI cross linking, all F(ab')$_2$ fragments were converted to Fab fragments by reduction/alkylation. Resulting Fab fragments did not activate human platelets when tested up to several fold higher concentrations at which intact IgG activates human platelets.

EXAMPLE 2

GPVI Specific Antibodies are Potent Inhibitors of Collagen-Induced Platelet Aggregation and Adhesion The inhibitory potential of the Fab fragments prepared according to Example 1 was tested on collagen-induced platelet functions, including collagen-induced platelet aggregation and adhesion of platelets to immobilized collagen under static and flow conditions.

The antibodies were tested for in vitro platelet aggregation as follows. A collagen dosing experiment was first performed to determine the amount of collagen that would give 70-90% platelet aggregation within 5 minutes of its addition because collagen response varies among individuals. Moreover, the type of collagen used in the assays can dramatically affect the response. From experience, acid insoluble equine tendon collagen (Nycomed, Germany) provided the greatest platelet aggregation response. Nieswandt (J. Biol. Chem. 275:23998-24002, 2000, and U.S. Patent Publication No. 2002/0141992), Lecut et al. (J. Thrombosis and Haemostasis 1:2653-2662, 2003), and Moroi et al. (Thromb. Haemost. 89:996-1003, 2003) also used acid insoluble equine tendon collagen, whereas others used a less responsive form of collagen, for example, bovine collagen type I fibers (Smethurst et al., Blood 103:903-911, 2004, and WO 03/054020). In the assays exemplified below, 1-4 µg/ml acid insoluble equine tendon collagen (Nycomed, Germany) was used to examine the inhibitory effect of a particular Fab preparation on platelet aggregation. The type of collagen used is same as that used in Qian et al. (Human Antibodies 11:97-105, 2002), WO 01/00810, WO 02/080968, and their related applications; but as discussed below, the GPVI antibodies of the present invention exhibit significantly greater inhibitory effect compared to the GPVI antibodies disclosed in Qian, WO 01/00810, and WO 02/080968.

The platelet aggregation assay was performed by collecting blood in $\frac{1}{10}$ volume of 3.8% trisodium citrate as an anticoagulant (Nakamura et al., J. Biol. Chem. 273(8):4338-44, 1998). Platelet rich plasma (PRP) was obtained by centrifugation of whole blood at 180×g for 15-20 minutes at room temperature. Platelets were counted and adjusted to 3-4×10$^8$ platelets/ml in platelet poor plasma prior to performing platelet aggregation studies. All experiments were performed within 3-4 hrs after blood collection and PRP was maintained at room temperature the entire time. Aggregation studies were performed in a four channel aggregometer AG10 (Kowa, Japan) which measures the kinetics of particle formation by laser scattering and aggregation by light transmission at 650 nm in the visible region of the light spectrum. PRP was incubated at 37° C. with varying amounts of Fab fragments for 10 minutes (5 minutes without stirring followed by additional 5 minutes with stirring) prior to the addition of acid insoluble equine tendon collagen (Nycomed, Germany) and aggregation was monitored for an additional 5-10 minutes.

Platelet adhesion to collagen under static conditions was examined using a modified procedure of Nakamura et al., J. Biol. Chem. 273:4338-4334 (1998) described earlier. Briefly, washed platelets were incubated with desired amounts of Fab fragments for 30 minutes in the presence and absence of Mg$^{2+}$ at room temperature prior to their addition to collagen-coated wells (2 µg/well with acid insoluble equine tendon collagen) (Nycomed, Germany). After 60-90 minutes of incubation at room temperature, unadhered platelets were removed by gentle washing with buffered saline and the adhesion was quantified by determining the LDH content of adhered platelets using a commercially available LDH kit (Promega, Mass.).

Platelet adhesion to immobilized collagen under flow conditions was measured in a flow chamber developed by Glycotech (Rockville, Md.). Whole blood, anticoagulated with recombinant hirudin (50 units/ml), was incubated with a solution containing Fab fragment for 15 minutes at 37° C. prior to being drawn through a collagen-coated (5 µg/cm² acid insoluble equine tendon collagen) (Nycomed, Germany) flow chamber at high shear (2600 sec$^{-1}$, 2 min). Unadhered platelets were washed with phosphate buffered saline and the adhered platelets were fixed with glutaraldehyde (0.5% w/v, 1 h) and stained with toludine blue/sodium borate (0.05%, 5 min). Surface coverage by platelets was estimated by digital image analysis. The average from 10 non-overlapping images was used to determine percentage surface area coverage.

Of the antibodies selected, Fab fragments from four IgGs, OM1, OM2, OM3, and OM4, inhibited collagen-induced platelet aggregation on human platelets. See Tables 2, 3, and 4. The order of inhibitory potency of the Fab fragments against collagen-induced platelet aggregation was OM1>OM2>OM3>OM4. Average $IC_{50}$ and SD values of each antibody for inhibition of collagen-induced platelet aggregation are shown in Table 4.

Cross reactivity of each antibody to rat, dog, and monkey platelets were also tested. Monkey and dog blood was purchased from Covance Research Inc, Vienna, Va. Sprague Dowley rats were obtained from Charles River Laboratories, Willmington, Mass. All four Fab fragments inhibited collagen-induced aggregation of monkey platelets. Interestingly, OM4 cross-reacted with rat platelets. These GPVI specific antibodies are useful tools for testing the effect of GPVI specific antibodies in animal models. Hybridomas producing OM1, OM2, OM3, and OM4 antibodies were deposited with the American Type Culture Collection (Manassas, Va.) on Apr. 29, 2004, as ATCC Nos. PTA-5938, PTA-5939, PTA-5940, and PTA-5941, respectively.

TABLE 4

Effect of Anti-GPVI Fab Fragments on Collagen-Induced Aggregation of Human Platelets and Cross-Reactivity to Non-Human Platelets

| Fab Fragment ID | $IC_{50}$ (µg/ml)* | | Cross reactivity** | | |
|---|---|---|---|---|---|
| | Average | SD | Rat | Dog | Monkey |
| OM1 | 0.575 | 0.049 | (−) | (−) | (+) |
| OM2 | 1.69 | 0.506 | (−) | (−) | (+) |
| OM3 | 3.02 | 0.768 | (−) | (−) | (+) |
| OM4 | 7.0 | 5.5 | (+) | (−) | (+) |
| ReoPro ® | 1.71 | 0.345 | (−) | (+) | (+) |
| 7E3 F(ab')$_2$ | n/d*** | n/d | (+) | n/d | n/d |

*Dose response curve were obtained using platelets from 3 different subjects. $IC_{50}$ values were calculated by non-regression analysis. Values are average ± SD from 3 experiments.
**Cross reactivity with animal platelets was based on the ability of individual Fab fragments to inhibit collagen-induced platelet aggregation and by positive rightward shift in FACS analysis. A (+) sign indicates inhibition of collagen-induced aggregation by Fab fragments and positive rightward shift while a (−) sign indicates no reaction in both tests.
***Not determined For comparison, REOPRO® (Centocor, Inc.), a widely used human-mouse chimeric anti-GPIIb-IIIa Fab fragment, and a F(ab')$_2$ fragment of the anti-GPIIb-IIIb monoclonal antibody 7E3 (Coller and Scudder, Blood 66:1456-1459, 1985), was tested on several of the same donors under the same conditions used to test the GPVI specific antibodies. REOPRO® inhibited collagen-induced platelet aggregation at an $IC_{50}$ of 1.71 µg/ml. Thus, OM1 possessed greater inhibitory potential than REOPRO®, while OM2 was equipotent to REOPRO®. REOPRO® was 2-4 times more potent than OM3 and OM4 in this assay. 7E3 F(ab')$_2$ cross-reacted with rat platelets, whereas REOPRO® did not (see Table 4).

Figure 2:
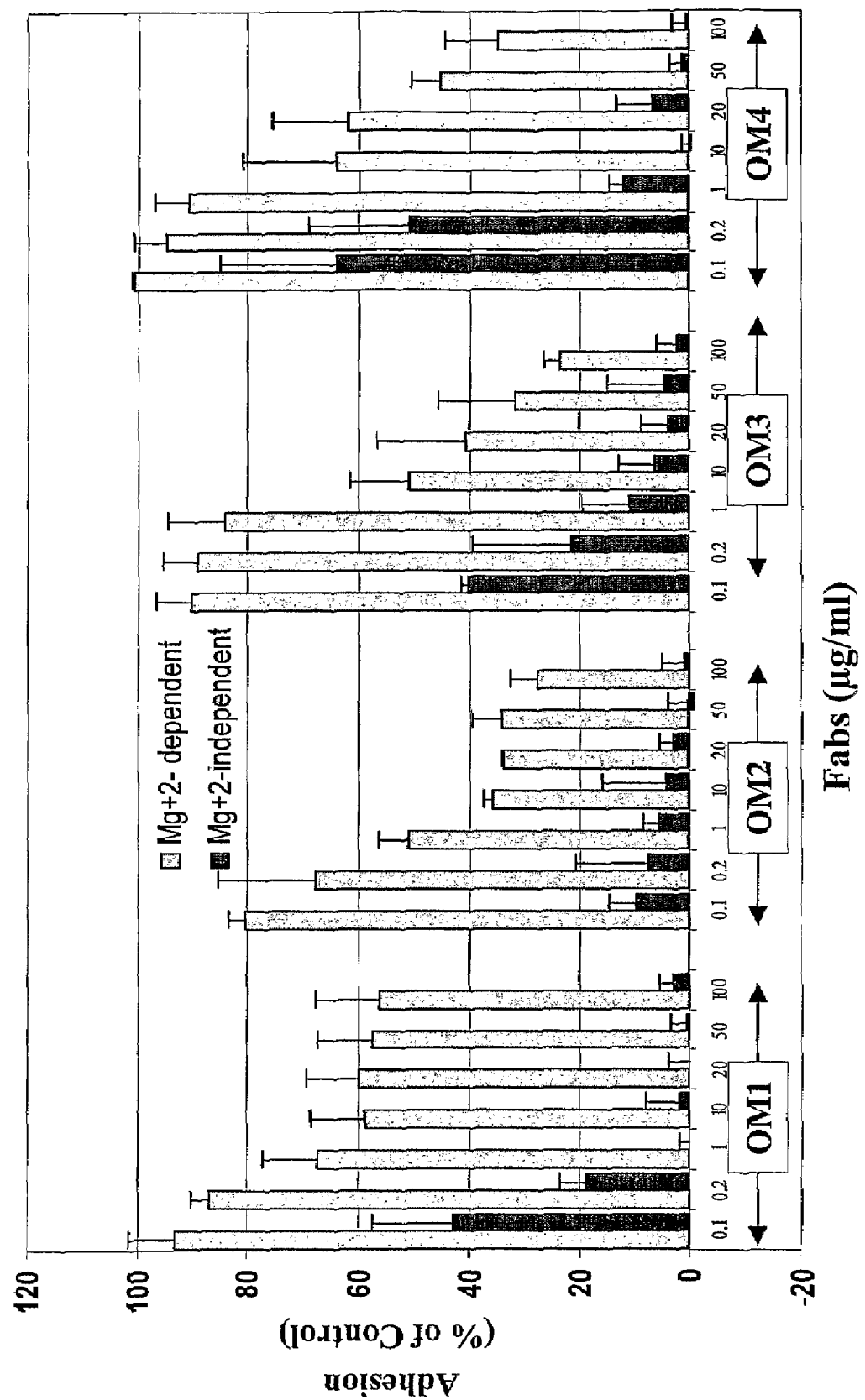
FIG. 2 is a bar graph showing the effects of Fab fragments of OM1, OM2, OM3, and OM4 at 0.1-100 µg/ml on platelet (human) adhesion to fibrillar collagen under static conditions.

The effect of Fab fragments on platelet adhesion under static conditions was also tested. Adhesion was carried out in the presence (GPIa-IIa and GPVI-dependent) and absence (GPVI-dependent) of $Mg^{2+}$. $Mg^{2+}$-independent adhesion is solely dependent on the presence of GPVI and was inhibited by all four Fabs at relatively low concentrations ($IC_{50}$ ranging from 0.1-1 µg/ml) as shown in FIG. 2. OM1, OM2, and OM3 had similar inhibitory activity ($IC_{50}$ range 0.1-0.2 µg Fabs/ml) while OM4 required a slightly higher dose to achieve similar inhibition ($IC_{50}$ range 0.2-1 µg Fabs/ml). The $Mg^{2+}$-dependent adhesion process required relatively higher doses of Fab fragments than those required for the $Mg^{2+}$-independent adhesion process (see FIG. 2). However, none of the Fabs were able to completely block the $Mg^{2+}$-dependent adhesion of platelets to collagen.

Figure 3:
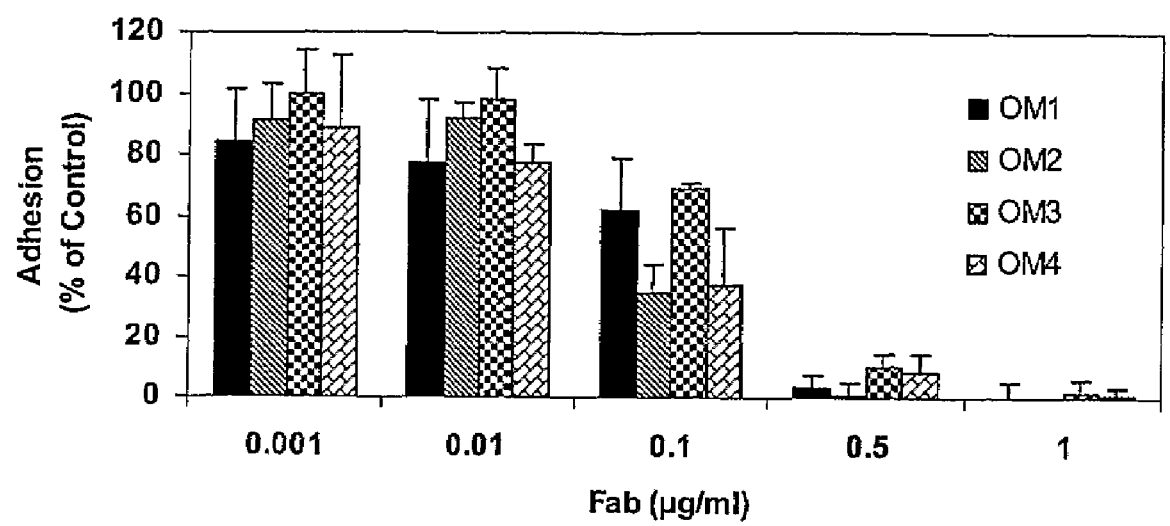
FIG. 3 is a bar graph showing the effects of Fab fragments of OM1, OM2, OM3, and OM4 at 0.001-1 µg/ml on $Mg^{2+}$-independent (GPVI-dependent) human platelet adhesion to fibrillar collagen under static conditions.

The effect of Fab fragments on $Mg^{2+}$-independent platelet adhesion under static conditions was repeated using even lower doses (0.001-1 µg Fabs/ml). As shown in FIG. 3, OM2 and OM4 Fab fragments inhibited platelet adhesion by 40-60% at 0.1 µg Fab/ml and OM1 and OM3 Fab fragments inhibited adhesion by 10-20% at the same concentration. This discrepancy may be due to batch variation and donor variability. In conclusion, the OM series of Fab fragments effectively inhibit GPVI-dependent ($Mg^{2+}$-independent adhesion) at concentrations lower than 0.5 µg/ml.

Figure 4:
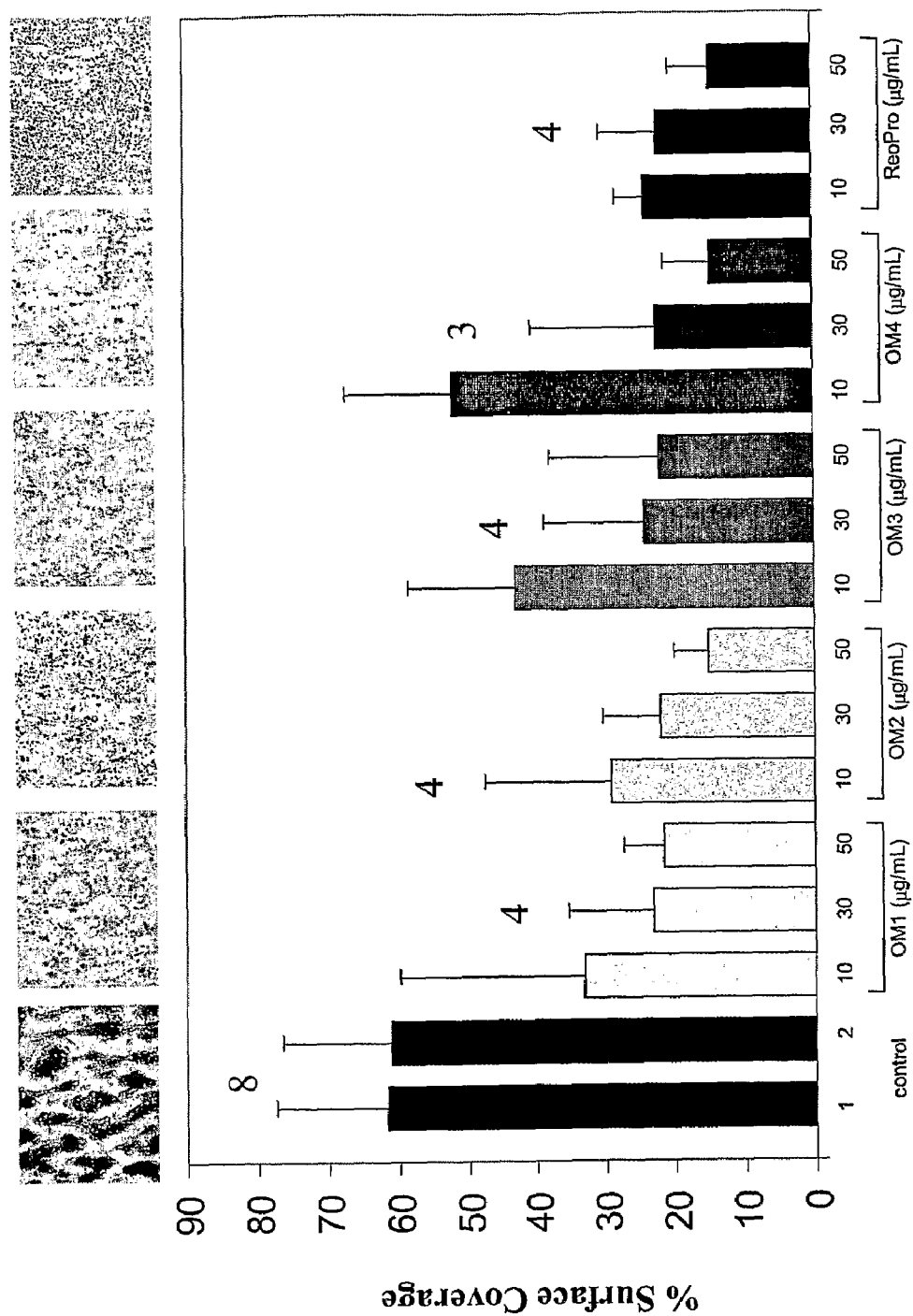
FIG. 4 illustrates the effects of Fab fragments of OM1, OM2, OM3, OM4, and REOPRO® on platelet (human) adhesion to acid insoluble collagen under high shear stress (2600 $sec^{-1}$) conditions.

The inhibitory effect of anti-GPVI Fab fragments on platelet adhesion was also tested under conditions closer to in vivo situations, as described above. Fab fragments of OM1, OM2, OM3, OM4 significantly inhibited platelet adhesion to immobilized collagen under high shear conditions (2600 sec$^{-1}$). Compared to a control sample, anti-GPVI Fabs induced dramatic changes in the size and morphology of the aggregates (FIG. 4). In comparison, REOPRO® (Centocor, Inc.) also prevented the formation of aggregates but a uniform layer of single platelets was observed on collagen fibers (FIG. 4).

The morphology of the aggregates is a result of two events: (1) the area covered by primary monolayer of platelets and (2) subsequent formation of aggregates thus adding a volume dimension to the over all picture. The dramatic reduction in aggregate formation along with surface coverage by the anti-GPVI Fab suggests that GPVI is not only involved in the primary adhesion process but that it also plays an important role in post-adhesion events, including platelet activation and subsequent thrombus growth.

Aggregation and adhesion assays demonstrate that the Fab fragments of GPVI specific antibodies of the invention, such as OM1, OM2, OM3, and OM4, are potent inhibitors of platelet functions. They are more potent at inhibiting collagen-induced platelet aggregation than the Fab fragment of the mouse monoclonal antibody 9O12.2 generated from mice immunized with a cDNA encoding recombinant soluble GPVI-Fc (rsGPVI-Fc) fusion protein as described in Lucet et al. (J. Thrombosis and Haemostasis 1:2653-2662, 2003), WO 02/80968, and US Patent Publication 2004/0253236. Additionally, the OM antibodies are more potent at inhibiting $Mg^{2+}$-independent adhesion to collagen than the 9O12.2 Fab fragment.

Nieswandt (J. Biol. Chem. 275:23998-24002, 2000, and U.S. Patent Publication No. 2002/0141992) reported a rat monoclonal antibody to mouse GPVI, JAQ1. However, saturating concentrations of JAQ1 (20 µg/ml) only displayed a limited inhibitory effect on collagen-induced platelet aggregation (see U.S. Patent Publication 2002/0141992, paragraph 29). Furthermore, JAQ1 did not recognize human GPVI in FACS analysis or Western blotting in our hands or in others (see Takayama et al., J. Thrombosis and Hemostasis 14: 75-81, 2003).

Others have generated single chain Fvs (ScFvs). For example, Qian et al. (Human Antibodies 11:97-105, 2002) reported a single chain Fv (ScFv) antibody of GPVI that had an $IC_{50}$ of 80-90 µg/ml in a collagen-induced platelet aggregation study using 2 µg/ml of the same collagen used in the present invention. Thus, the GPVI specific antibodies of the invention are significantly more potent in inhibiting collagen-induced platelet aggregation compared with Qian et al. ScFvs also reported in WO 01/00810, WO 02/80968, and their related applications required a significantly greater concentration (110-150 µg/ml of ScFv) for inhibiting collagen-induced platelet aggregation compared with the GPVI specific antibodies of the present invention.

Similarly, Smethurst et al. (Blood 103:903-911, 2004, and WO 03/054020), reported a ScFv antibody of GPVI that had an $IC_{50}$ of 12-16 µg/ml in collagen-induced platelet aggregation. In comparison, OM1, OM2, OM3 and OM4 are more potent than Smethurt's ScFv. Additionally, although U.S. Pat. Nos. 6,245,527 and 6,383,779 disclose anti-GPVI antibodies, they do not provide any examples of anti-GPVI antibodies that are as potent at inhibiting collagen-induced platelet aggregation as those of the present invention.

EXAMPLE 3

GPVI Specific Antibodies Inhibit Collagen-Induced Secretion and Thromboxane $A_2$ Formation Fab fragments of the GPVI specific antibodies of the invention were also tested for their effect on collagen-induced secretion and thromboxane $A_2$ ($TXA_2$) formation. Secretion refers to agonist-induced release of bioactive contents from alpha and dense granules from platelets.

One way to quantify agonist-induced release is to measure ATP content in the medium by luciferase assay using chemiluminescence method. Platelet-rich plasma (PRP) was tested for collagen-induced ATP secretion using a Lumi-aggregometer (Chronolog Corporation, PA) and a luciferase-luciferin reagent. The Lumi-aggregometer simultaneously measures the agonist-induced platelet aggregation and ATP secretion. Briefly, human blood was drawn directly into 3.8% trisodium citrate with a syringe (9:1 volume blood:citrate). Platelet-rich plasma (PRP) was prepared by centrifugation at 180×g for 15 minutes. PRP (360 µl) was mixed with 40 µl luciferase-luciferin reagent (Chrono-lume; Chronolog Corporation, PA) and the mixture was incubated with varying amounts of test Fabs, REOPRO®, or control for 5 minutes at 37° C. 1-4 µg/ml of collagen (acid insoluble equine tendon collagen) (Nycomed, Germany) was added at five minutes and aggregation and ATP secretion were monitored for eight minutes. At the end of the reaction (10-11 minutes), a known amount of ATP solution was added to obtain a deflection which was used to calculate the ATP amount secreted by platelets upon agonist challenge.

Thromboxane $A_2$ formation were measured in parallel samples used above. Ten minutes after the collagen addition step above, 500 µL of stop solution (50 mM EDTA, 2 mM Indomethacin in 130 mM NaCl) was added to 200 µL of PRP to terminate thromboxane $A_2$ formation. The suspension was centrifuged at 1,000×g for 10 min at 4° C. The supernatant was saved and frozen at −20° C. until tested for thromboxane $B_2$, which is a stable metabolite of thromboxane $A_2$. Thromboxane $B_2$ was quantified by using a commercially available kit (Thromboxane $B_2$ Biotrak Assay, Amersham).

All Fab fragments of OM1, OM2, OM3, and OM4 antibodies potently inhibited collagen-induced ATP release from human platelets (Table 5). OM1 showed inhibition of more than 90% at 1 µg/mL. OM2, OM3, and OM4 also attained inhibition of more than 90% at 3 µg/mL. REOPRO® was less effective at inhibiting ATP secretion than the anti-GPVI antibodies, suggesting that anti-GPVI Fabs are better inhibitors of collagen-induced ATP release. Secondary agonists released from platelets are known to synergize thrombus growth. Therefore, inhibitors of collagen-induced secretion, such as the GPVI specific antibodies of the invention, are potent inhibitors of thrombus growth.

TABLE 5

Effect of Anti-GPVI Fab Fragments on Collagen-Induced ATP Release From Human Platelets*

| antibody | concentration (µg/mL) | % inhibition (mean ± SD) |
| --- | --- | --- |
| OM1 | 1 | 97.6 ± 2.1 |
|  | 3 | 96.8 ± 6.3 |
| OM2 | 1 | 63.6 ± 41.6 |
|  | 3 | 97.7 ± 2.7 |
| OM3 | 1 | 72.8 ± 23.7 |
|  | 3 | 94.2 ± 0.4 |
| OM4 | 1 | 50.0 ± 29.5 |
|  | 3 | 91.3 ± 5.2 |
| ReoPro ® | 1 | 18.0 ± 13.5 |
|  | 3 | 56.9 ± 31.7 |

*Results were obtained from 4 different platelet donors.

Collagen-induced thromboxane $A_2$ generation was also strongly inhibited by Fab fragments of OM1, OM2, OM3, and OM4 (Table 6). Among the four Fab fragments tested, OM1 showed inhibition of more than 90% at 1 µg/mL. OM2 and OM3 also attained inhibition of more than 90% at 3 µg/mL. OM4 inhibited thromboxane $A_2$ formation by about 86% at 3 µg/mL. In contrast, REOPRO® showed little or no inhibitory effect on thromboxane $A_2$ formation at 1 and 3 µg/mL. It has also been shown that blockade of GPVI inhibits the generation of $TXA_2$ and expression of an activated IIb-IIIa complex on collagen-adhered platelets (Nakamura et al., J. Biol. Chem. 273:4338, 1998; Nakamura et al., J. Biol. Chem. 274:11879, 1999). Therefore, inhibition of $TXA_2$ generation by anti-GPVI Fab fragments suggests that the GPVI specific antibodies of the invention inhibit the upstream signalling events leading to the expression of activated IIb-IIIa complex and ultimately, followed by an attenuation in thrombus growth.

TABLE 6

Effects of Fab Fragments of Anti-GPVI Antibodies on Collagen-Induced Thromboxane $A_2$ Formation in Human Platelets*

| antibody | concentration (µg/mL) | ng/3 × $10^8$ platelets (mean ± SD) |
| --- | --- | --- |
| control |  | 104.3 ± 37.4 |
| OM1 | 1 | 5.0 ± 3.4 |
|  | 3 | 2.9 ± 2.7 |
| OM2 | 1 | 31.5 ± 36.5 |
|  | 3 | 5.0 ± 3.3 |

TABLE 6-continued

Effects of Fab Fragments of Anti-GPVI Antibodies on Collagen-Induced Thromboxane $A_2$ Formation in Human Platelets*

| antibody | concentration (µg/mL) | ng/3 × 10⁸ platelets (mean ± SD) |
|---|---|---|
| OM3 | 1 | 24.1 ± 10.6 |
|  | 3 | 6.9 ± 4.8 |
| OM4 | 1 | 28.7 ± 8.1 |
|  | 3 | 14.5 ± 4.9 |
| ReoPro ® | 1 | 77.8 ± 35.1 |
|  | 3 | 106.7 ± 70.9 |

*Results were obtained using platelets from 4 different donors

EXAMPLE 4

Binding Affinities and Reactivity of Fab Fragments of Anti-GPVI Antibodies to GPVI Binding affinities were determined according to the method of Fujimura et al. Thromb Haemost 87:728-34 (2002). $^{125}$I-labeled antibodies used in the determination of binding affinities were prepared from unlabeled IgGs according to the Iodo-beads method (Pierce, Ill.). Briefly, one Iodo-bead was soaked for 5 minutes in iodination buffer containing 0.5 mCi carrier-free Na$^{125}$I (Amersham) followed by the addition of a candidate IgG (100 µg). After 5 minutes of incubation at room temperature, the reaction mixture was applied to a PD10 column (Amersham) to separate $^{125}$I-bound IgG from free iodine. Fractions containing $^{125}$I-IgG were eluted from the column and a small volume (1 µl) was subjected to TCA precipitation. Both the precipitated pellets and the resulting supernatants were counted in a gamma counter to quantify the incorporation of $^{125}$I in IgG. Fractions with maximal counts in the precipitate (<95%) were pooled and read in a spectrophotometer at 280 nm to determine protein concentration. A known volume was recounted in a gamma counter to obtain specific activity of the labeled IgG. The specific activity among various antibodies ranged from 0.33-0.97 µCi/ug IgG.

Binding affinities were determined by incubation of washed human platelets (5×10⁸/ml) with 1 nM $^{125}$I-IgG in the presence and absence of various concentrations of unlabelled homologous IgG (0-500 nM) for 1 hr. The free and bound radioactivities were separated by layering the mixture over BSA (10% solution in saline) solution and centrifuged at 15,000×g for 10 minutes. After careful removal of both the supernatant and the BSA cushion, the tip of the tube was cut and radioactivity of the pellet was counted in a gamma counter. Eight to ten triplicate-point competition binding isotherms were developed for evaluating the binding of individual IgG. The data was analyzed using the non-linear regression analysis software, Prism (GraphPad Software Inc. CA).

Binding affinity experiments revealed that all four antibodies bound avidly to platelets with affinities ranging from 0.7-1.7 nM (Table 7). The antibodies of the invention were compared with the binding affinities of antibodies reported in the art: REOPRO® (Kd=6.25±2.6×10$^{-9}$M) (from Sassoli et al., Thromb Haemost 85:868-902, 2001), scFv-10B12 (Kd=7.9×10$^{-7}$M) (from Smethurst et al., Blood 103:903-91, 2004), and 9O12.2-IgG (Kd=18×10$^{-9}$M) (from WO 02/080968). REOPRO® and scFv-10B12 are monovalent fragments whereas the OM series used in this example and 9O12.2 are IgGs. All four OM antibodies bound with higher affinity to human platelets than reported for REOPRO®, scFv-10B12, and 9O12.2-IgG (Table 7). Monovalent fragments generally have somewhat reduced affinities compared with their corresponding intact IgG; however, that reduction would not be expected to be significant.

TABLE 7

Binding Affinities of Anti-GPVI Antibodies

| Antibody ID | Kd | µg IgG/ml |
|---|---|---|
| OM1 | 1.724 ± 0.22 × 10$^{-9}$M | 0.258 ± 0.033 |
| OM2 | 0.723 ± 0.093 × 10$^{-9}$M | 0.108 ± 0.0103 |
| OM3 | 0.8187 ± 0.14 × 10$^{-9}$M | 0.1220 ± 022 |
| OM4 | 0.785 ± 0.25 × 10$^{-9}$M | 0.117 ± 0.037 |
| ReoPro ®* | 6.25 ± 2.6 × 10$^{-9}$M | 0.31 ± 0.13 |
| scFv - 10B12** | 7.9 × 10$^{-7}$M | 23.7 |
| 9O12.2 - IgG*** | 18 × 10$^{-9}$M | 2.7 |

The binding study of the OM series is from a single experiment using platelets from different individuals. Each data point was run in triplicate.
*Data from Sassoli et al. Thromb Haemost 85: 868-902 (2001).
**Data from Smethurst et al., Blood 103: 903-911 (2004). 10B12 is a human specific scFv antibody against GPVI obtained from a phage display method.
***Data from WO 02/080968. 9O12.2 is a monoclonal anti-GPVI antibody.

Western blotting analysis was performed to determine the reactivity of the OM series antibodies to GPVI from various species. Platelets (1×10⁸/ml) from various species were solubilized in 2% SDS containing EDTA, EGTA, PMSF and NEM (1 mM each). Proteins were separated on 4-20% precast Tris-glycine gradient mini gels (Invitrogen, Carlsbad, Calif.), and the resolved proteins were transferred to nitrocellulose membranes (Invitrogen, Carlsbad Calif.). Individual lanes were cut and blocked with 5% skim milk in TBS-T (10 mM Tris.HCl pH 7.4, 150 mM NaCl, and 0.5% Tween 20) for 60 minutes. Nitrocellulose strips were incubated with OM antibodies (2 µg/ml) or biotinylated convulxin overnight at 4° C. Membranes were washed extensively with TBS-T and probed with either HRP-conjugated goat anti-mouse IgG (OM1, OM2, and OM4), HRP-conjugated goat anti-hamster IgG (OM3) or streptavidin-HRP (biotinylated convulxin) for 1 hr at room temperature. Membranes were washed three times with a large excess of TBS-T. Immune reactive bands were visualized using an enhanced chemiluminescence detection system (ECL-Amersham Pharmacia Biotech, Little Chalfont, UK).

Figure 5:
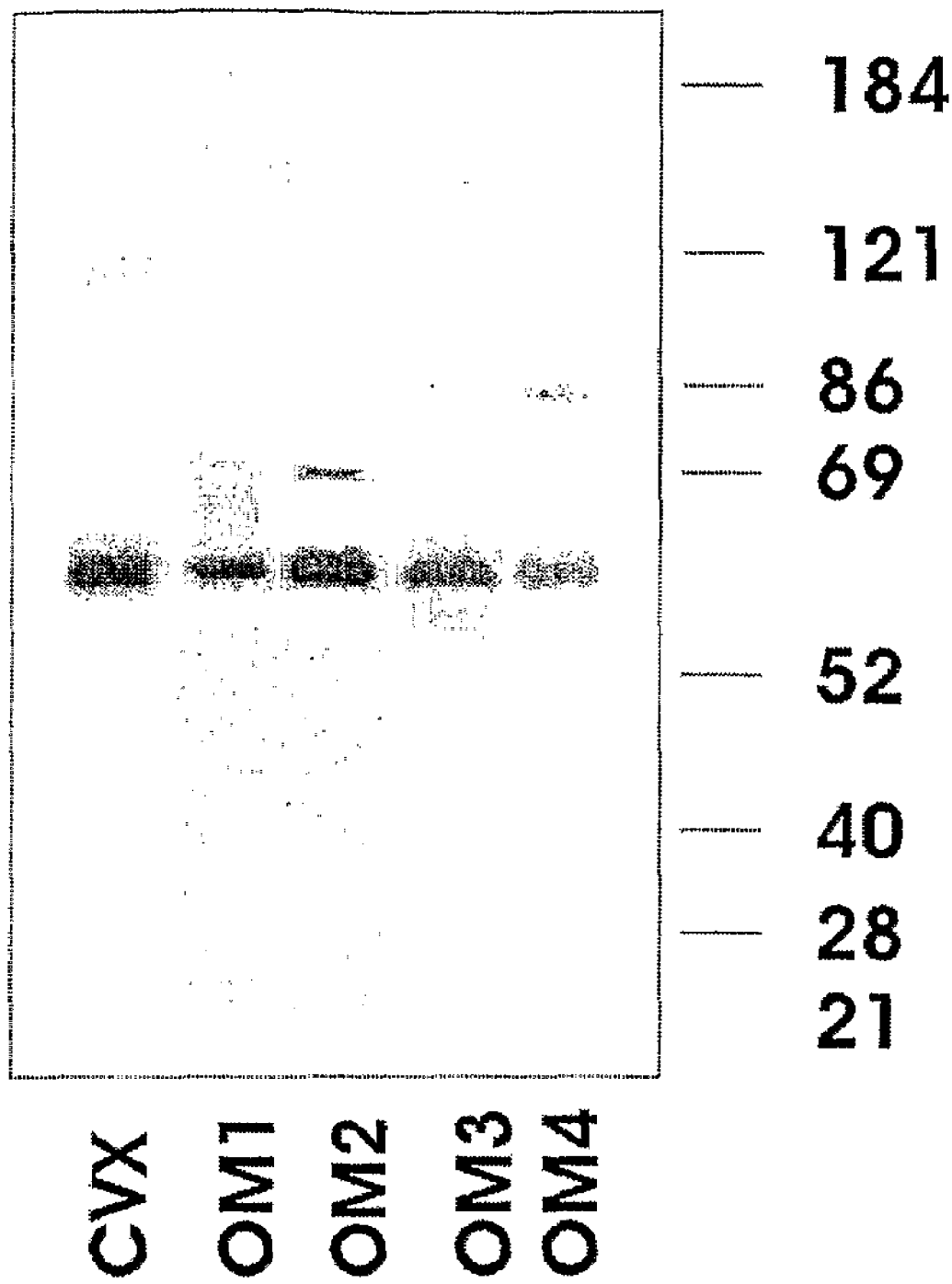
FIG. 5 is a Western blot of the OM series antibodies (OM1, OM2, OM3, and OM4) and convulxin (CVX) reacting with GPVI in human platelet lysate.

All four OM antibodies reacted with denatured GPVI from human platelets on immunoblots (FIG. 5). Similar reactivity was seen with monkey platelets (blots not shown). None of the antibodies reacted with mouse, pig, dog, rabbit or guinea pig platelets. Only OM4 reacted positively with rat platelet lysate. These data suggest that all of the OM series antibodies recognize GPVI in platelets from humans and monkeys while OM4 additionally recognizes GPVI in rat platelets.

EXAMPLE 5

Complementarity Determining Regions (CDRS)

The sequences of the complementarity determining regions (CDRs) of OM1, OM2, OM3 and OM4 were determined.

Total RNA was isolated from OM1, OM2, OM3, and OM4 hybridomas using TRIzol (Invitrogen). cDNA was synthesized with the SuperScript First-Strand System (Invitrogen) using random primers. DNA sequences corresponding to the variable regions of antibodies were then amplified by polymerase chain reaction using Platinum Pfx DNA Polymerase (Invitrogen) with Heavy Primers or Light Primers mix (Amersham). The amplified DNA was ligated into pCR4-TOPO vector (Invitrogen) and the resulting construct was transformed into chemically competent cells using the TOPO TA Cloning kit (Invitrogen). Transformed cells were cultured in the presence of kanamycin and the amplified plasmid was isolated using the E.Z.N.A. Plasmid Miniprep Kit II (Omega Bio-tek). Sequencing of inserted DNA was performed on the ABI PRISM 310 Genetic Analyser using the ABI PRISM BigDye Terminator v3.1 Cycle Sequencing Kit (Applied Biosystems). DNA sequences were analyzed and converted into amino acid sequences using the OMIGA 2.0 software (Oxford Molecular).

The CDRs of OM1, OM2, OM3, and OM4 are shown in Table 8.

TABLE 8

CDR Sequences of Anti-GPVI Antibodies

OM1

| H1: | SYWMN | (SEQ ID NO:1) |
| H2: | MIHPSDSETTLNQKFKD | (SEQ ID NO:2) |
| H3: | DDYYDSSSHALDY | (SEQ ID NO:3) |
| L1: | RASQSVSTSTYSYIY | (SEQ ID NO:4) |
| L2: | FASYLES | (SEQ ID NO:5) |
| L3: | QHIWEIPWTF | (SEQ ID NO:6) |

OM2

| H1: | DHYIS | (SEQ ID NO:7) |
| H2: | WIYPGYGNIRYNEKFKG | (SEQ ID NO:8) |
| H3: | SADGYFRYFDV | (SEQ ID NO:9) |
| L1: | RASGNIHNYLA | (SEQ ID NO:10) |
| L2: | NSEILAD | (SEQ ID NO:11) |
| L3: | QHFWTAPFTF | (SEQ ID NO:12) |

OM3

| H1: | DFYMN | (SEQ ID NO:13) |
| H2: | SISGGSSDIKYADVVKG | (SEQ ID NO:14) |
| H3: | WGDHWDLDY | (SEQ ID NO:15) |
| L1: | QASQNIGNELN | (SEQ ID NO:16) |
| L2: | GASSLYP | (SEQ ID NO:17) |
| L3: | KQDLNYPITF | (SEQ ID NO:18) |

OM4

| H1: | SFGMH | (SEQ ID NO:19) |
| H2: | FISSGSSTIYYADIVKG | (SEQ ID NO:20) |
| H3: | SGYANAMDY | (SEQ ID NO:21) |
| L1: | KASQDVSPAVT | (SEQ ID NO:22) |
| L2: | WASTRHT | (SEQ ID NO:23) |
| L3: | QQHYSFPWTF | (SEQ ID NO:24) |

EXAMPLE 6

GPVI and Thrombosis

The role of GPVI in thrombosis had been shown in a prior study using GPVI-depleted or FcRγ-KO/GPVI deficient mice (Nieswandt et al., The EMBO Journal 20:2120-2130 (2001)). Both the GPVI-depleted or FcRγ-KO/GPVI deficient mice lack the FcRγ chain. In this example, the involvement of GPVI in thrombosis was confirmed using GPVI-KO mice that do not lack the FcRγ chain.

Figure 6:
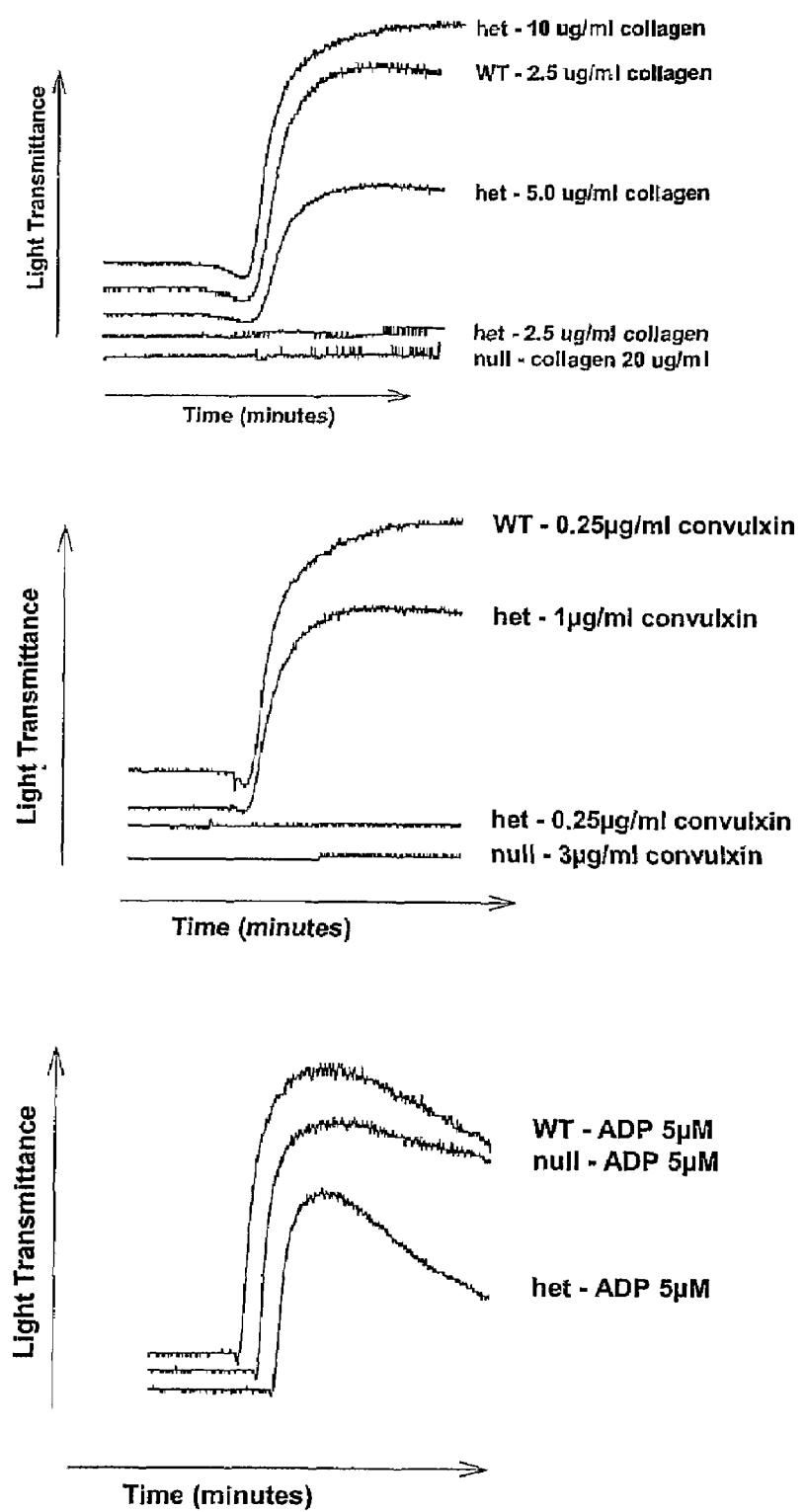
FIG. 6 illustrates the complete lack of platelet aggregation induced by collagen and convulxin in GPVI knock-out animals.

GPVI knock-out mice were developed as described above. Platelets from these mice failed to respond to high dose collagen (20 µg/ml) and to the GPVI-specific agonist, convulxin (3 µg/ml), but responded normally to ADP (5 µM) (FIG. 6). Heterozygous GPVI-deficient mice which produce half the amount of GPVI compared with wild-type showed reduced responses to collagen and convulxin but normal responses were observed upon increase in agonist dose (FIG. 6). These observations confirm the role of GPVI as a dominant collagen receptor on the platelet surface.

The role of GPVI in thrombosis and homeostasis was first tested by co-injection of collagen-epinephrine, which normally induces a lethal pulmonary thrombo-embolism (see Table 9). Mice were anaesthetized with ketamine/xylazine (150/15 mg/kg, IP) and a mixture of collagen and epinephrine (800/60 µg/kg) was injected into the right jugular vein. The animals were then observed for 15 minutes and categorized as follows: (a) animals that succumbed to death within 10 minutes of the injection, and (b) animals that survived showed transient respiratory distress, which alleviated within 10 minutes. The surgical wounds of surviving animals were sutured and the animals were returned to the animal facility. Approximately 83% (15 out of 18) of GPVI wild-type mice died within 5 minutes of injection. All heterozygous GPVI-deficient mice (18 out of 18) died within five minutes of injection. In contrast to wild-type and heterozygous animals, approximately 55% of the GPVI-KO mice (homozygous) survived the lethal injection of collagen and epinephrine, suggesting that GPVI plays an important role in pulmonary thromboembolism induced by the injection of collagen.

TABLE 9

The Role of GPVI in Pulmonary Thromboembolism

| Genotype | number of animals survived | % Survival |
| --- | --- | --- |
| Wild-type (+/+) | 3/18 | ~16 |
| Heterozygous (+/−) | 0/18 | 0 |
| Homozygous (−/−) | 10/18 | ~55 |

As shown in Table 10, GPVI knock-out mice had essentially same tail bleeding time as wild-type and heterozygous mice. Bleeding times of the GPVI knock-out mice were compared to those of knock-out mice deficient in β3 integrin, which is also found on platelets and is involved in platelet aggregation and thrombosis (Kairbaan et al., J. Clin. Invest. 103:229-238, 1999). In contrast to the GPVI-deficient mice, the homozygous β3 knock-out mice bled continuously. Therefore, administration of anti-GPVI Fab fragments in vivo may be safer as they should not significantly affect bleeding time because the bleeding time in GPVI-knockout mice is similar to that of wild-type mice.

TABLE 10

Tail Bleeding Time in Wild-Type, Heterozygous and Homozygous Mice: Comparison With β3 Knock-Out Mice

| Genotype | Tail bleeding time (seconds) | |
|---|---|---|
|  | GPVI-knock out | β3-knock out* |
| Wild-type (+/+) | 191 ± 186 (n = 9) | 156 ± 89 (n = 15) |
| Heterozygous (+/−) | 190 ± 193 (n = 14) | 156 ± 99 (n = 15) |
| Homozygous (−/−) | 165 ± 110 (n = 13) | >600 (n = 15)** |

Figure 7:
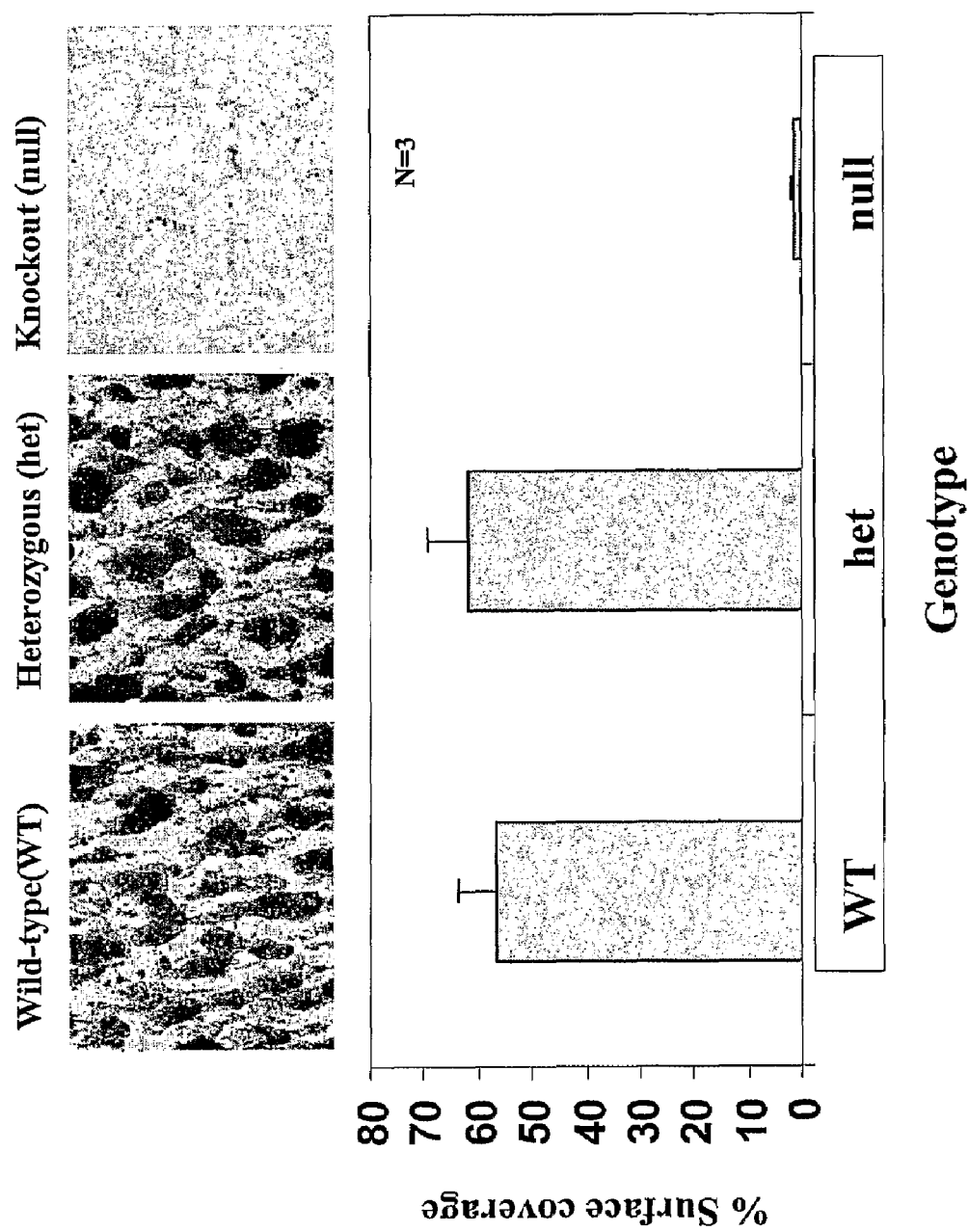
FIG. 7 illustrates the lack of interaction of platelets from GPVI knock-out mice to acid insoluble collagen under high shear stress conditions.

*J Clin Invest 103: 229, 1999
**Significantly different from wild-type and heterozygous mice. In most cases, bleeding had to be stopped manually to prevent death To further confirm the role of GPVI in thrombosis, whole blood from wild-type, heterozygous and GPVI-KO mice were perfused onto type I collagen-coated cover slips at a shear stress of 2600 sec-1. Platelets from GPVI-KO mice failed to adhere to collagen fibers while platelets from wild-type and GPVI-heterozygous mice adhered to collagen fibers and formed large thrombi. There was no difference in surface coverage and thrombus morphology between wild-type and GPVI-heterozygous mice (FIG. 7).

EXAMPLE 7

Effect of OM2 Fab Fragment on Ex Vivo Collagen-Induced Platelet Aggregation and Skin Bleeding Time in Cynomolgus Monkeys Dose-escalation study. The OM2 Fab fragment was further evaluated because it showed the strongest inhibitory effect among the OM antibodies in an in vitro collagen-induced platelet aggregation assay using platelets from Cynomolgus monkeys. The OM2 Fab fragment was administered by intravenous injection to Cynomolgus monkeys in escalating doses and its effect on ex vivo collagen-induced platelet aggregation and skin bleeding time were evaluated. REOPRO® was tested in a similar manner.

Under inhalation anesthesia, the OM2 Fab fragment or REOPRO® was injected intravenously into the cephalic vein of the forearm at 1 hr intervals. Thirty minutes after each injection, blood was collected for the measurement of collagen-induced platelet aggregation. Platelet rich plasma (PRP) and platelet poor plasma (PPP) were prepared by sequential centrifugation of blood that was anti-coagulated with trisodium citrate. Platelet aggregation was measured by the turbidimetric method 1 hr after blood collection. Concentrations of collagen used to induce platelet aggregation were between 5 and 20 μg/mL, depending on the responsiveness of the platelets from each monkey. Skin bleeding time was measured 30 min after each injection of the antibody by compressing the muscle of the forearm with a manchette at 40 mmHg and incising the skin with a Triplett Bleeding time device (Helena Laboratory). Blood flowing from the wound was absorbed with filter paper and bleeding time was measured until bleeding stopped, or at 1800 sec. Cumulative dose of antibody was used to evaluate the effects of the antibodies.

Figure 8:
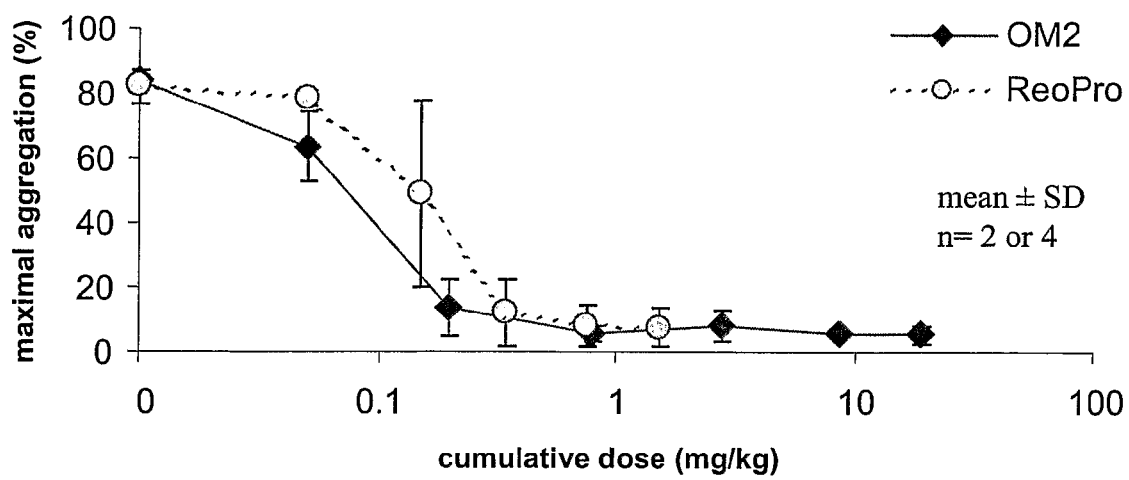
FIG. 8 is a graph showing the effect of the OM2 Fab fragment and REOPRO® on ex vivo collagen-induced platelet aggregation in Cynomolgus monkeys.

The OM2 Fab fragment exerted a dose-dependent inhibitory effect on collagen-induced platelet aggregation (FIG. 8). At the cumulative dose of 0.2 mg/kg or higher, the OM2 Fab fragment inhibited platelet aggregation by more than 80%.

REOPRO® also exerted a dose-dependent inhibitory effect on collagen-induced platelet aggregation (FIG. 8) but inhibited platelet aggregation by more than 80% at a cumulative dose of 0.35 mg/kg or higher.

Figure 9:
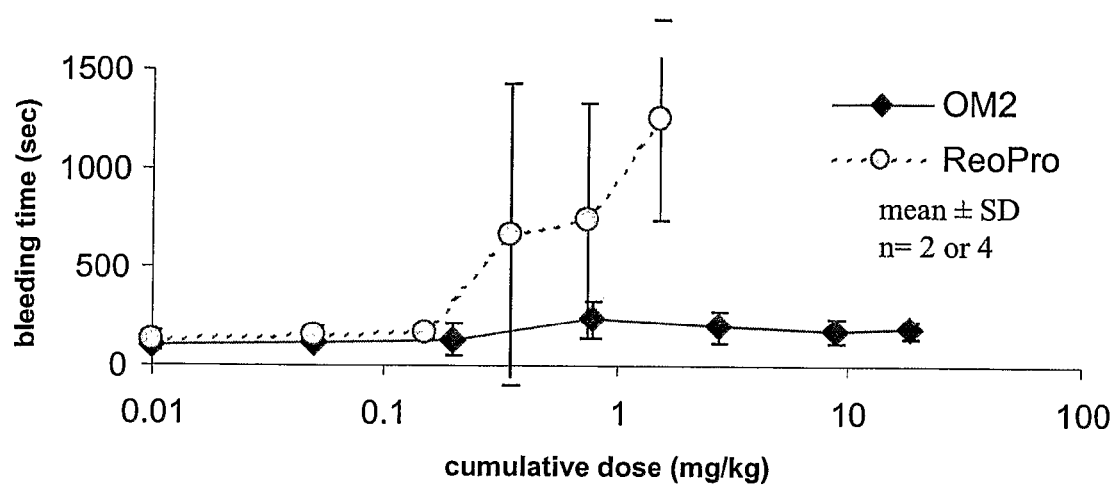
FIG. 9 is a graph showing the effect of the OM2 Fab fragment and REPOPRO® on skin bleeding time in Cynomolgus monkeys.

OM2 Fab fragment prolonged skin bleeding time only slightly (2.4 times the baseline value) at a cumulative dose of 0.8 mg/kg (FIG. 9). Although the OM2 Fab fragment slightly prolonged bleeding time at a cumulative dose of 18.8 mg/kg, bleeding time did not exceed the bleeding time observed at 0.8 mg/kg.

In contrast, REOPRO® prolonged skin bleeding time dramatically (FIG. 9). At a cumulative dose of 0.35 mg/kg, the average bleeding time was 5 times longer than the baseline value. Additionally, the prolongation of bleeding time by REOPRO® was dose-dependent. At a cumulative dose of 1.55 mg/kg, bleeding time was 9.5 times longer than baseline level.

In summary, the OM2 Fab fragment showed an equally potent inhibitory effect on ex vivo collagen-induced platelet aggregation as exhibited by REOPRO®. However, the effect of OM2 Fab fragment on skin bleeding time was much milder than that of REOPRO®. These results suggest that blockade of GPVI has a superior risk/benefit ratio when compared to that of GPIIb/IIIa blockade and therefore may be better suited for clinical treatment. Moreover, a red spot was observed at the injection site in one monkey after administration of REOPRO® at 0.4 and 0.8 mg/kg. Although this spot disappeared after several days, no abnormalities were observed after OM2 Fab administration.

Pharmacodynamics study. The change in the effects of the OM2 Fab fragment over time on ex vivo collagen-induced platelet aggregation and skin bleeding time was evaluated in three Cynomolgus monkeys after bolus intravenous injection. The change in effects by REOPRO® was similarly evaluated.

The dose of 0.4 mg/kg was selected for this study because the OM2 Fab fragment and REOPRO® inhibited ex vivo collagen-induced platelet aggregation at 0.2 mg/kg and 0.35 mg/kg, respectively. After bolus intravenous injection of antibody into the cephalic vein of the forearm, blood was collected at 1, 2, 3, 6 and 24 hrs. Platelet aggregation was measured 1 hr after each blood collection as described above under the dose-escalation study. Concentrations of collagen used to induce platelet aggregation were 5 or 10 μg/mL in this study, depending on the responsiveness of the platelets from each monkey. Bleeding time was also measured at 1, 2, 3, 6 and 24 hrs after antibody administration as described under the dose-escalation study.

Figure 10:
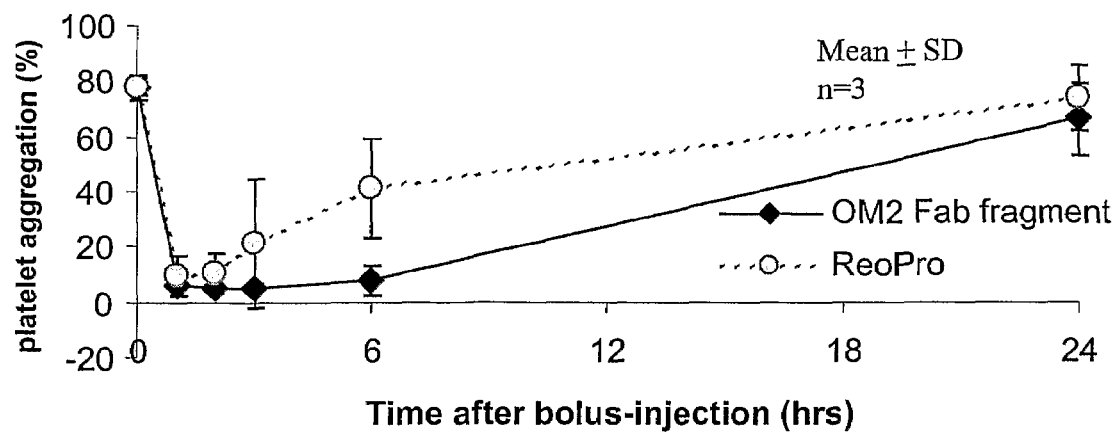
FIG. 10 is a graph showing the anti-aggregation effect of the OM2 Fab fragment and REPOPRO® over time after bolus injection (0.4 mg/kg) in Cynomolgus monkeys.

The OM2 Fab fragment injected at 0.4 mg/kg inhibited ex vivo collagen-induced platelet aggregation by more than 80% at 1, 2, 3 and 6 hrs after administration (FIG. 10). At 24 hrs after injection, platelet aggregation recovered nearly to basal level.

Similarly, REOPRO® injected at 0.4 mg/kg inhibited ex vivo collagen-induced platelet aggregation by more than 80% at 1 and 2 hrs after administration (FIG. 10). However, in contrast to the OM2 Fab fragment, platelet aggregation recovered in a time-dependent manner: 73% inhibition at 3 hr, 47% inhibition at 6 hr and 6% inhibition at 24 hr after administration.

Figure 11:
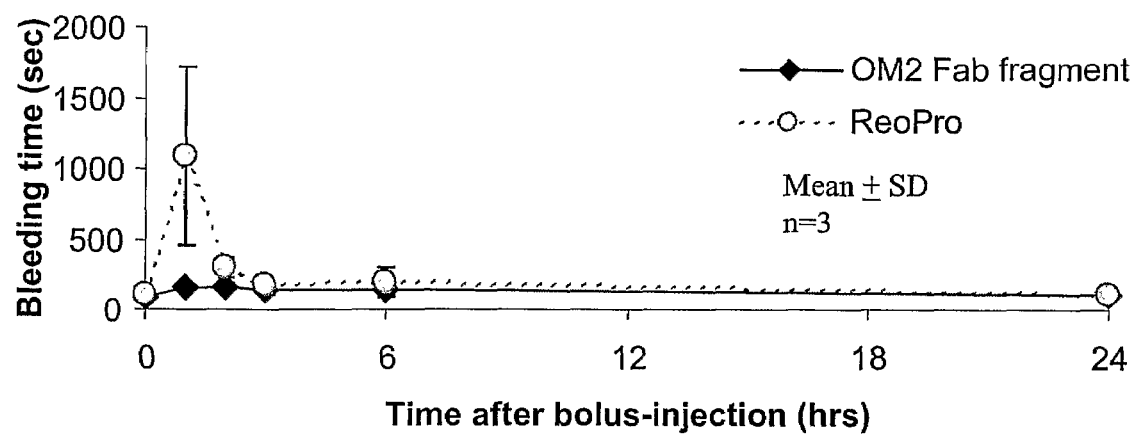
FIG. 11 is a graph showing the time-course effect of the OM2 Fab fragment and REPOPRO® on skin bleeding time after bolus injection (0.4 mg/kg) in Cynomolgus monkeys.

As shown in FIG. 11, the OM2 Fab fragment slightly prolonged skin bleeding time between 1 and 6 hrs after administration (1.7 to 2.0 times longer than baseline level). Bleeding time returned to nearly baseline level at 24 hrs after injection, coincident with the recovery of platelet aggregation.

In contrast, REOPRO® significantly prolonged bleeding time at 1 hr after administration (10.7 times longer than baseline level) (FIG. 11). Prolongation of bleeding time became less prominent in a time-dependent manner.

These results showed that the inhibitory half-life of the OM2 Fab fragment on platelet aggregation is longer than that of REOPRO®. In addition, these results again suggest that the risk/benefit ratio of the OM2 Fab fragment is superior to that of REOPRO®.

EXAMPLE 8

Effect of OM4 Fab Fragment on Ex Vivo Collagen-Induced Platelet Aggregation, Bleeding Times, and Platelet Count in Rats The OM4 Fab fragment was further tested for ex vivo collagen-induced platelet aggregation, tail and nail bleeding time in rats. For comparison, the 7E3 F(ab')$_2$ fragment derived from an established murine antibody raised against human platelet glycoprotein complex GPIIb/IIIa (Collar et al. J. Clin Invest. 72:325-338, 1983) was tested in a similar manner. 7E3 IgG was obtained from large cultures using a 7E3 hybridoma obtained from the ATTC. F(ab')$_2$ fragments were prepared as described in Collar et al J. Clin Invest. 72:325-338, 1983. In preliminary studies using rats, the optimal dose of OM4 Fab and 7E3 F(ab')$_2$ were determined to be 20 and 10 mg/kg, respectively. The ex vivo collagen-induced platelet aggregation remained inhibited by OM4 Fab for 30 minutes after which the inhibition reversed at 60-90 minutes, suggesting a fast clearance of OM4 Fab in rats. All observations were made at 20 minutes after the administration of vehicle, test and reference antibody.

Adult male Sprague-Dawley rats were anesthetized with ketamine/xylazine. Heparin-filled catheters were inserted into the femoral vein, femoral artery, and carotid artery for drug administration, blood pressure/heart rate recording, and blood sampling, respectively. After the equilibration period, a small sample of blood (~1.2 mL, anticoagulated with 10 U/mL heparin) was withdrawn from the carotid artery for determination of platelet count. The degree of platelet aggregation elicited by 1 µg/mL collagen was measured using a whole blood aggregometer (Chrono-log, Havertown, Pa.). Nail-bleeding time was also determined at this time by cutting one of the hind limb toenails at a point that transected the nail pulp and by absorbing the blood every 15 sec onto a piece of filter paper, without touching the cut surface of the nail. Nail-bleeding time was defined as the time elapsed between cutting the nail and the point at which no further blood absorbed onto the filter paper.

Vehicle, OM4 Fab, or 7E3 F(ab')$_2$ composition was administered into the femoral vein. At 20 minutes, a second blood sample was withdrawn for aggregometry and platelet count determination, as described above. Immediately following withdrawal of the final sample, nail and tail bleeding times were determined. Tail-bleeding time was determined by removing the terminal 3 mm of the tail using a sharp scalpel blade and immersing the distal 2-3 cm tail into 37° C. saline. Tail-bleeding time was defined as the time elapsed between cutting the tail and the point at which no more blood drew from the cut surface of the tail. Six rats were used for each group (vehicle, OM4 Fab and 7E3 F(ab')$_2$ fragment).

Figure 12:
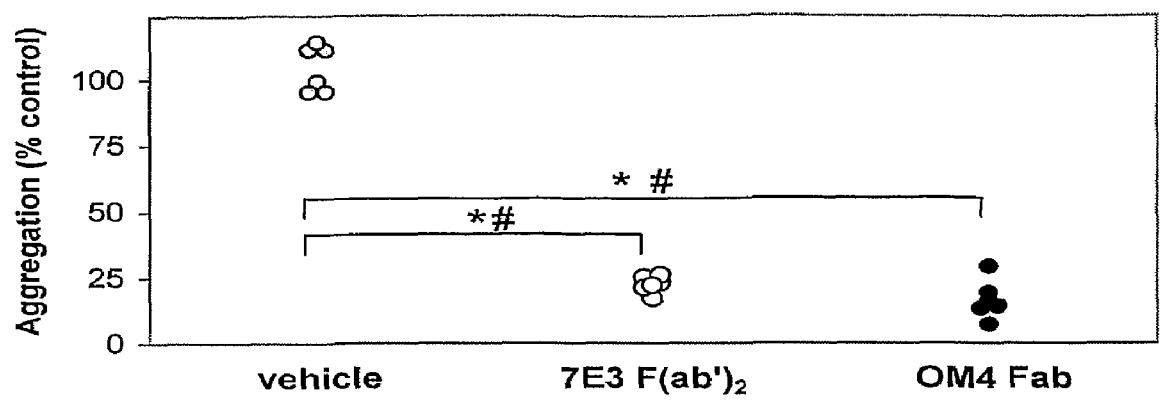
FIG. 12 illustrates the effects of the OM4 Fab and 7E3 F(ab')$_2$ fragments on ex vivo collagen-induced platelet aggregation in rats.

Both OM4 Fab and 7E3 F(ab')$_2$ fragments produced a statistically significant degree of inhibition of platelet aggregation at 20 min after the administration of the antibody fragments, in relation to the vehicle (P<0.05) (FIG. 12). The inhibition was highly reproducible, although the variability was slightly greater in the OM4 Fab group. Blood pressure and body core temperature remained unchanged by the intravenous administration of vehicle, OM4 Fab, and 7E3 F(ab')$_2$ fragment compounds.

Nail bleeding time was dramatically prolonged by the administration of the 7E3 F(ab')$_2$ fragment while the administration of OM4 Fab had no effect in four out of six animals tested (FIG. 13A). In two animals, the nail bleeding time was prolonged to 26 and 31 minutes by the administration of OM4 Fab. In contrast, the 7E3 F(ab')$_2$ fragment prolonged nail bleeding time beyond 30 minutes in all cases except one in which nail bleeding halted at 18 minutes (FIG. 13A). The mean nail bleeding time in animals receiving 7E3 F(ab')$_2$ fragment was significantly greater than OM4 Fab and vehicle groups, as indicated by the Student's t-test. OM4 Fab did not induce any significant prolongation of nail bleeding time when compared to vehicle.

Figure 14:
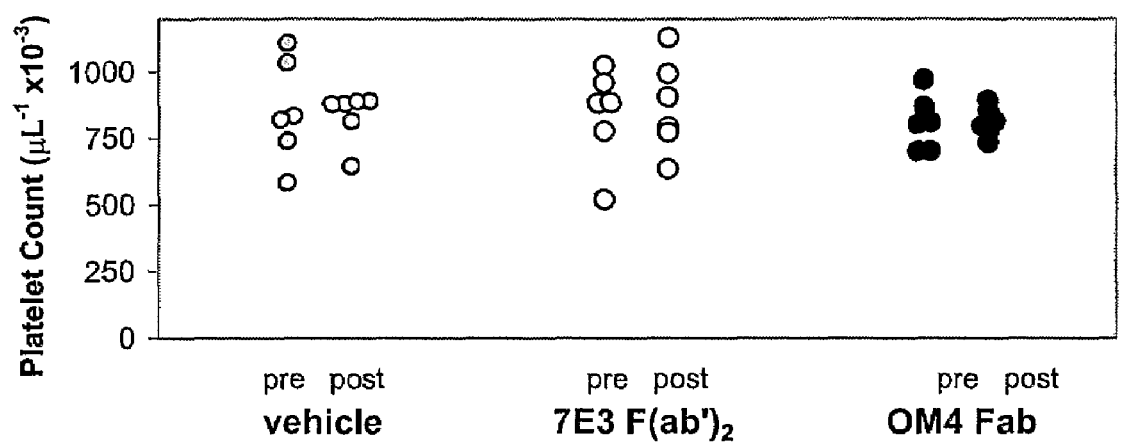
FIG. 14 illustrates the effects of the OM4 Fab and 7E3 F(ab')$_2$ fragments on platelet count in rats.

Similar to the nail bleeding time, tail bleeding time was dramatically prolonged in all animals by the administration of 7E3 F(ab')$_2$ fragment while administration of OM4 Fab had no effect in four out of six animals tested (FIG. 13B). In two animals, the tail bleeding time was prolonged to 26 and >30 minutes. In contrast, the 7E3 F(ab')$_2$ fragment prolonged tail bleeding time to beyond 30 minutes in all cases (FIG. 13B). There was no significant effect of intravenous administration of vehicle, OM4 Fab and 7E3 F(ab')$_2$ fragment on platelet count (FIG. 14).

The data obtained from this study clearly shows that OM4 Fab (20 mg/kg) and 7E3 F(ab')$_2$ fragment (10 mg/kg) elicit similar degrees of inhibition of collagen-induced platelet aggregation but 7E3 F(ab')$_2$ significantly prolonged bleeding time. OM4 Fab's ability to inhibit platelet function without significantly affecting bleeding time suggests that it would be therapeutically beneficial. OM4 Fabs may provide similar positive benefits as currently available platelet inhibitors without their negative bleeding side effects.

EXAMPLE 9

Effect of OM4 Fab Fragment in a Rat Arterial Thrombosis Model

The effect of the OM4 Fab fragment was also studied in an in vivo arterial thrombosis model in rats. Although various models of in vivo thrombosis have been reported in the literature, a model developed by Folts (see e.g., Circulation 83(6 Suppl):IV 3-14, 1991) has been widely used to test the efficacy of antithrombotic agents. This original model was developed in a canine coronary artery but for this study, the model was modified for testing on rat carotid artery. Briefly, the carotid artery was mechanically injured, followed by stenosis. Combination of vascular injury and narrowing of the blood vessel (two conditions mimicking the pathogenesis of thrombosis, i.e. arteriosclerosis and stenosis) results in the formation of a thrombus. The thrombus can then be mechanically dislodged and reformed by removal and replacement of the vascular occluder, respectively. This leads to cyclic flow reduction (CFR) as discussed in more detail below. Antithrombotic agents may reduce the number of CFR or completely prevent the formation of CFR.

Rats were anesthetized with pentobarbital (50 mg/kg, i.p.) and mechanically ventilated with an intubation of the tracheal. A segment of the femoral vein was dissected and used for drug injection. The carotid artery was exposed via a midline incision in the ventral cervical area and dissected free of connective tissue. A small flow probe (Transonic, 1RB, Transonic Systems Inc., Ithaca, N.Y.) was placed distally on the artery to measure blood flow. Thrombosis was induced by applying two conditions. First, an injury was induced by three consecutive cross-clamps of the middle exposed segment of the artery for 10 seconds each, with a needle holder having one ratchet click closed. Second, a 50% reduction of the baseline blood flow was applied by inflating a vascular occluder (1.5 mm inner diameter, In Vivo Metric, Healdsburg, Calif.), which consists of a C-shaped balloon that was placed on the site of the injury. Blood flow was gradually reduced to zero within about 2-5 minutes due to the formation of a thrombus. The thrombus was physically dislodged by deflating the balloon, and blood flow was immediately restored. One CFR is counted when the blood flow reduces to zero after the 50% blood flow reduction and when blood flow is restored. After re-applying the 50% flow reduction, blood flow again gradually decreased, resulting in the next CFR as a new thrombus formed. The number of CFRs was counted during a 30 min observation period. The number was also rounded to a half cycle.

In the pre-injury groups, either saline or OM4 Fab fragment at 20 mg/kg was given by an intravenous bolus injection 2 min before mechanical injury was applied. CFRs were then recorded for 30 min.

In the post-injury groups, CFRs were initiated by endothelial injury and 50% reduction of flow. CFRs were observed for 15 min followed by an intravenous bolus injection of vehicle or OM4 Fab fragment at 20 mg/kg. CFRs were then recorded for 30 min.

An un-paired t-test was used to compare the number of CFRs in saline and OM4 pre- or post-treated groups. $P<0.05$ was considered significant.

Pre-iniury groups. OM4 Fab fragment injected at 20 mg/kg before mechanic injury reduced the number of CFRs from 10.5±4.1 (mean±SD) to 4.1±5.2 (FIG. 15A). This reduction was statistically significant ($p<0.02$, t-test).

Post-injury groups. OM4 Fab fragment injected at 20 mg/kg injected after establishing CFR also reduced the number of CFRs from 12.2±3.8 to 3.5±3.6 (FIG. 15B). This reduction was also statistically significant ($p<0.003$, t-test). This result demonstrates that the OM4 Fab fragment can inhibit thrombus formation even after initiation of the interaction between platelets and subendothelial collagen. Moreover, these results suggest that anti-GPVI antibodies can potently inhibit in vivo arterial thrombosis formation induced by endothelial injury/blood flow perturbation that are proposed triggers of thrombotic diseases in clinical situations.

EXAMPLE 10

Relationship Between the Occupancy Rate of GPVI and Inhibition of Collagen-Induced Platelet Aggregation The relationship between GPVI occupancy rate on the platelet surface and the inhibitory effect on collagen-induced platelet aggregation by biotinylated OM2 Fab fragment in human platelets in vitro was examined.

OM2 Fab fragment was biotinylated with Sulfo-NHS-LC-Biotin (Pierce). Biotin solution (150 µL, 10 mg/mL in distilled water) was added to OM2 Fab fragment solution in PBS (5 mg, 2 mg/mL). Reaction tube was incubated on ice for 2 hrs. To remove free biotin, the reaction mixture was dialyzed against saline in a cold room overnight.

Blood was collected from 3 healthy donors in 1/10 volume of 3.8% trisodium citrate anticoagulant and platelet rich plasma (PRP) obtained by centrifugation at 180×g for 15 min at room temperature. Platelets were counted and adjusted to $3\times10^8$ platelets/mL with platelet poor plasma. Measurement of aggregation was performed within 4 hrs of blood collection. Aggregation studies were performed in an AG10 aggregometer (Kowa, Japan). PRP was incubated with biotinylated OM2 Fab fragment (0, 0.1, 0.3, 0.5, 0.7, 1, 3, 10 and 20 µg/mL) for 10 min at 37° C. before collagen was added and aggregation was monitored for an additional 5-10 min. The collagen dose required to induce 70-90% aggregation was determined for each donor prior to the evaluation of the antibody.

PRP ($3\times10^8$ platelets/mL, 400 µL each) was incubated with biotinylated OM2 Fab fragment (0, 0.1, 0.3, 0.5, 0.7, 1, 3, 10 and 20 µg/mL) for 10 min at room temperature. Then, washed platelets were prepared as follows. PRP was supplemented with 1 µg/mL $PGE_1$, 1 mM EDTA, and EGTA and centrifuged at 2,000×g for 10 min. After discarding plasma, the platelet pellet was suspended in platelet wash buffer (PWB: phosphate-buffered saline supplemented with 1 mM EDTA and EGTA, 0.1% $NaN_3$, 100 ng/mL $PGE_1$ and 0.35% BSA, pH 7.4). Then, platelets were centrifuged and washed again. The washed platelets were suspended in a small volume of PWB and platelets were counted. Finally, the washed platelets ($1\times10^8$ platelets/mL) were solubilized by mixing with an equal volume of 1% Triton X-100-containing phosphate-buffered saline.

Biotinylated OM2 Fab fragment was quantified by the ELISA method using streptavidin (Pierce, 21125) as a capture reagent and goat anti-mouse IgG antibody-HRP (American Qualex, A106PU) as a detecting reagent.

In all three donors, collagen-induced platelet aggregation was inhibited by more than 75% by biotinylated OM2 Fab fragment at a concentration of 3 µg/mL.

Figure 16:
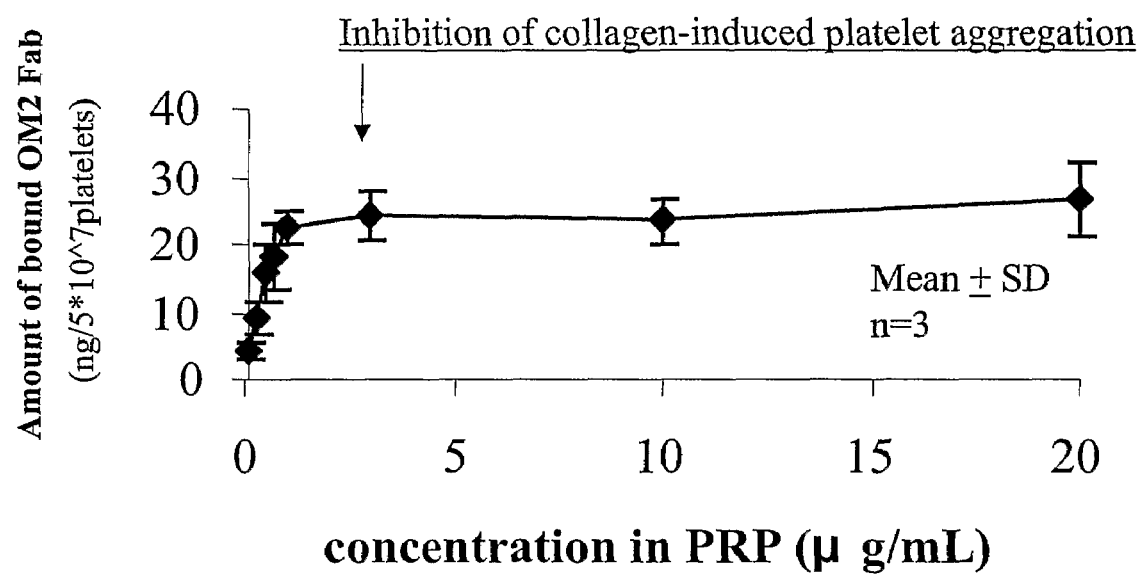
FIG. 16 is a graph showing the concentration-dependent binding of biotinylated OM2 Fab fragment to human platelets in vitro.

In the occupancy rate assay, occupancy rate was assumed to be at 100% at 20 µg/mL of biotinylated OM2 Fab fragment (bound amount: 26.4±5.5 ng/$5\times10^7$ platelets). As shown in FIG. 16, the amount of bound OM2 Fab fragment saturated at 3 µg/mL (24.3±3.5 ng/$5\times10^7$ platelets). The occupancy rate of biotinylated OM2 Fab fragment at 3 µg/mL was 92%. This result suggests that an occupancy rate of more than 90% of GPVI on platelet surface is required to exert maximal inhibitory effects on collagen-induced platelet aggregation.

In conclusion, the GPVI specific antibodies of the invention may be useful antithrombotic agents. As demonstrated above, the GPVI specific antibodies are potent inhibitors of platelet functions induced by collagen.

The specification is most thoroughly understood in light of the teachings of the references cited within the specification, all of which are hereby incorporated by reference in their entirety. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A monoclonal antibody specific for a glycoprotein VI (GPVI) polypeptide or peptide, wherein the monoclonal antibody inhibits collagen-induced platelet aggregation at an $IC_{50}$ of less than 7 µg/ml, wherein the $IC_{50}$ is determined using a concentration of collagen that induces 70-90% platelet aggregation within 5 minutes of its contact with platelets in a platelet aggregation assay, wherein the monoclonal antibody specifically binds to a GPVI polypeptide or peptide at a Kd of lower than $10^{-8}$M, and wherein the monoclonal antibody is selected from OM1 (ATCC No. PTA-5938), OM2 (ATCC No. PTA-5939), OM3 (ATCC No. PTA-5940), and OM4 (ATCC No. PTA-5941).

2. The monoclonal antibody of claim 1, wherein the monoclonal antibody is OM1.

3. The monoclonal antibody of claim 1, wherein the monoclonal antibody is OM2.

4. The monoclonal antibody of claim 1, wherein the monoclonal antibody is OM3.

5. The monoclonal antibody of claim 1, wherein the monoclonal antibody is OM4.

6. An antithrombotic composition comprising a pharmaceutically effective amount of at least one monoclonal antibody of claims 1-5 and a pharmaceutically acceptable excipient.

7. A method of making an antithrombotic composition comprising admixing at least one monoclonal antibody of claims 1-5 in a pharmaceutically acceptable excipient.

8. A kit comprising at least one dose of a pharmaceutically effective amount of at least one monoclonal antibody of claims 1-5 in a container.

* * * * *